(12) United States Patent
Sewell et al.

(10) Patent No.: US 11,078,252 B2
(45) Date of Patent: *Aug. 3, 2021

(54) T-CELL RECEPTOR

(71) Applicant: University College Cardiff Consultants Ltd., Cardiff South Glamorgan (GB)

(72) Inventors: Andrew Sewell, Cardiff South Glamorgan (GB); Garry Dolton, Cardiff South Glamorgan (GB)

(73) Assignee: University College Cardiff Consultants Ltd., Cardiff South Wales (GB)

(*) Notice: Subject to any disclaimer, the term of this patent is extended or adjusted under 35 U.S.C. 154(b) by 0 days.

This patent is subject to a terminal disclaimer.

(21) Appl. No.: 17/153,329

(22) Filed: Jan. 20, 2021

(65) Prior Publication Data

US 2021/0147506 A1 May 20, 2021

Related U.S. Application Data

(63) Continuation of application No. 16/858,082, filed on Apr. 24, 2020, which is a continuation-in-part of application No. PCT/GB2018/053045, filed on Oct. 22, 2018.

(30) Foreign Application Priority Data

Oct. 26, 2017 (GB) .................................. 1717578
Apr. 16, 2018 (GB) .................................. 1806155

(51) Int. Cl.
| | | |
|---|---|---|
| C07K 14/705 | (2006.01) | |
| C07K 14/725 | (2006.01) | |
| A61K 35/17 | (2015.01) | |
| A61K 45/06 | (2006.01) | |
| C12N 7/00 | (2006.01) | |
| A61K 38/00 | (2006.01) | |

(52) U.S. Cl.
CPC .......... *C07K 14/7051* (2013.01); *A61K 35/17* (2013.01); *A61K 45/06* (2013.01); *C12N 7/00* (2013.01); *A61K 38/00* (2013.01); *C12N 2740/15043* (2013.01)

(58) Field of Classification Search
CPC .................................................. C07K 14/7051
See application file for complete search history.

(56) References Cited

U.S. PATENT DOCUMENTS

2020/0369742 A1* 11/2020 Sewell .................. A61K 35/17

FOREIGN PATENT DOCUMENTS

WO    WO-2018162563 A1    9/2018

OTHER PUBLICATIONS

Chua et al., "Endogenous MHC-related protein 1 is transiently expressed on the plasma membrane in a conformation that activates mucosal-associated invariant T cells," Journal of Immunology 2011; 186: 4744-4750.
Crowther et al., "Genome-wide CRISPR-Cas9 screening reveals ubiquitous T cell cancer targeting via the monomorphic MHC class I-related protein MR1," Nature Immunology 2020; 178-185.
Crowther et al., "Supplementary Information: Genome-wide CRISPR-Cas9 screening reveals ubiquitous T cell cancer targeting via the monomorphic MHC class I-related protein MR1," Nature Immunology 2020: 9 pages.
Eckle et al., "A molecular basis underpinning the T cell receptor heterogeneity of mucosal-associated invariant T cells," 2014, The Journal of Experimental Medicine, 2014; 211(8): 1585-1600.
Ekeruche-Makinde et al., "T-cell receptor-optimized peptide skewing of the T-cell repertoire can enhance antigen targeting," J. Biol. Chem. 2012; 287(44) 37269-37281 plus Suppl. Tables.
Gold et al., "MR1-restricted MAIT cells display ligand discrimination and pathogen selectivity through distinct T cell receptor usage," The Journal of Experimental Medicine 2014; 211(8): 1601-1610.
Goldfinch et al., "Conservation of mucosal associated invariant T (MAIT) cells and the MR1 restriction element in ruminants, and abundance of MAIT cells in spleen," Veterinary Research 2010; 41(5): 62.
Guo et al., "Adoptive T Cell Therapy Targeting CD1 and MR1," Frontiers in Immunology 2015; 247(6).
International Search Report for International Application No. PCT/GB2018/053045, dated Jan. 30, 2019, 5 pages.
Laugel et al., "Engineering of Isogenic Cells Deficient for MR1 with a CRISPR/Cas9 Lentiviral System: Tools to Study Microbial Antigen Processing and Presentation to Human MR1-Restricted T Cells," Journal of Immunology 2016; 197: 971-982.
Lepore et al., "Functionally diverse human T cells recognize non-microbial antigens presented by MR1," eLife 6:e24476.
Li et al., "MAGeCK enables robust identification of essential genes from genome-scale CRISPR/Cas9 knockout screens," Genome Biology 2014; 15: 554.
Lissina et al., "Protein kinase inhibitors substantially improve the physical detection of T-cells with peptide-MHC tetramers," Journal of Immunological Methods 2009; 340: 11-24.
Parra-Cuadrado et al., "A study on the polymorphism of human MHC class I-related MR1 gene and identification of an MR1-like pseudogene," Tissue Antigens 2000; 56(2): 170-172.

(Continued)

*Primary Examiner* — Scott Long
(74) *Attorney, Agent, or Firm* — Dechert LLP; Andrew T. Wilkins

(57) ABSTRACT

The present disclosure relates to a new T-cell receptor (TCR), in particular at least one complementarity-determining region (CDR) thereof; a T-cell expressing said TCR; a clone expressing said TCR; a vector encoding said TCR; a soluble version of said TCR; a pharmaceutical composition or bispecific comprising said TCR, said cell, said clone or said vector; use of said TCR or said cell or said clone or said vector or said pharmaceutical composition or bispecific to treat cancer; and a method of treating cancer using said TCR, said cell, said clone, said vector, said pharmaceutical composition or bispecific comprising said TCR.

30 Claims, 24 Drawing Sheets

Specification includes a Sequence Listing.

(56) References Cited

OTHER PUBLICATIONS

Patel et al., "Identification of essential genes for cancer immunotherapy," Nature 2017; 548: 537-542.

Reantragoon et al., "Antigen-loaded MR1 tetramers define T cell receptor heterogeneity in mucosal-associated invariant T cells," The Journal of Experimental Medicine 2013; 210: 2305-2320.

Ryan et al., "Cleavage of foot-and-mouth disease virus polyprotein is mediated by residues located within a 19 amino acid sequence," Journal of General Virology 1991; 72: 2727-2732.

Sanjana et al., "Improved vectors and genome-wide libraries for CRISPR screening," Nature Methods 2014; 11:783-784.

Shalem et al., "Genome-scale CRISPR-Cas9 knockout screening in human cells," Science 2014; 343: 84-87.

Theaker et al., "T-cell libraries allow simple parallel generation of multiple peptide-specific human T-cell clones," J. Immunol. Methods 2016; 430: 43-50.

Tungatt et al., "Antibody stabilization of peptide-MHC multimers reveals functional T cells bearing extremely low-affinity TCRs," Journal of Immunology 2015; 194: 463-474.

Vacchini et al., "MR1-restricted T cells are unprecedented cancer fighters," Front. Immunol. 2020: 11: 751.

Won et al., "Clinical relevance of circulating mucosal-associated invariant T cell levels and their anti-cancer activity in patients with mucosal-associated cancer," Oncotarget 2016; 7(46): 76274-76290.

Wooldridge et al., "MHC Class I Molecules with Superenhanced CD8 Binding Properties Bypass the Requirement for Cognate TCR Recognition and Nonspecifically Activate CTLs," The Journal of Immunology 2010; 184: 3357-3366.

Wooldridge et al., "A single autoimmune T cell receptor recognizes more than a million different peptides," Journal of Biological Chemistry 2012; 287: 1168-1177 plus Suppl. Data.

\* cited by examiner

MC.7.G5 TCR alpha chain TRAV38.2/DV8 TRAJ31 (CDRs underlined in bold text)

AQTVTQSQPEMSVQEAETVTLSCTYDTSESDYYLFWYKQPPSRQMILVIRQEAYKQQ
NATENRFSVNFQKAAKSFSLKISDSQLGDAAMYFCAYRSAVNARLMFGDGTQLVV
KPNIQNPDPAVYQLRDSKSSDKSVCLFTDFDSQTNVSQSKDSDVYITDKCVLDMRSM
DFKSNSAVAWSNKSDFACANAFNNSIIPEDTFFPSPESS

MC.7.G5 TCR beta chain TRBV25.1 TRBJ2.3 (CDRs underlined in bold text)

EADIYQTPRYLVIGTGKKITLECSQTMGHDKMYWYQQDPGMELHLIHYSYGVNSTE
KGDLSSESTVSRIRTEHFPLTLESARPSHTSQYLCASSEARGLAEFTDTQYFGPGTRLT
TVLEDLKNVFPPEVAVFEPSEAEISHTQKATLVCLATGFYPDHVELSWWVNGKEVHS
GVCTDPQPLKEQPALNDSRYALSSRLRVSATFWQDPRNHFRCQVQFYGLSENDEWT
QDRAKPVTQIVSAEAWGRAD

Figure 3

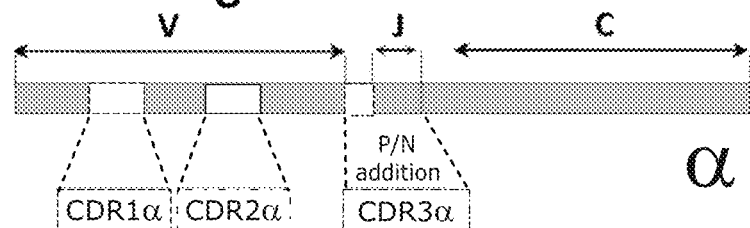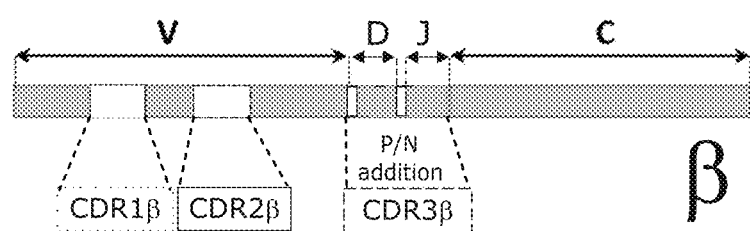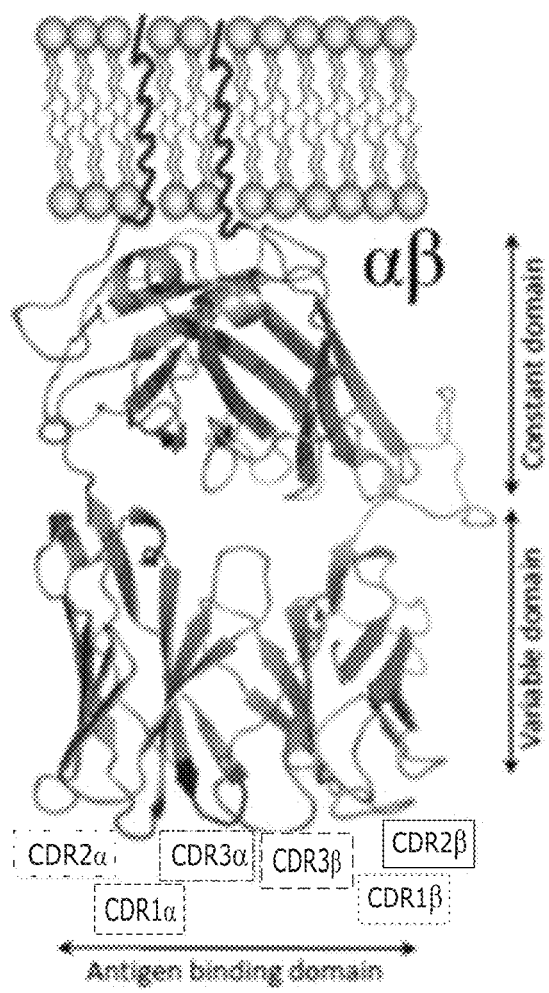
Figure 12

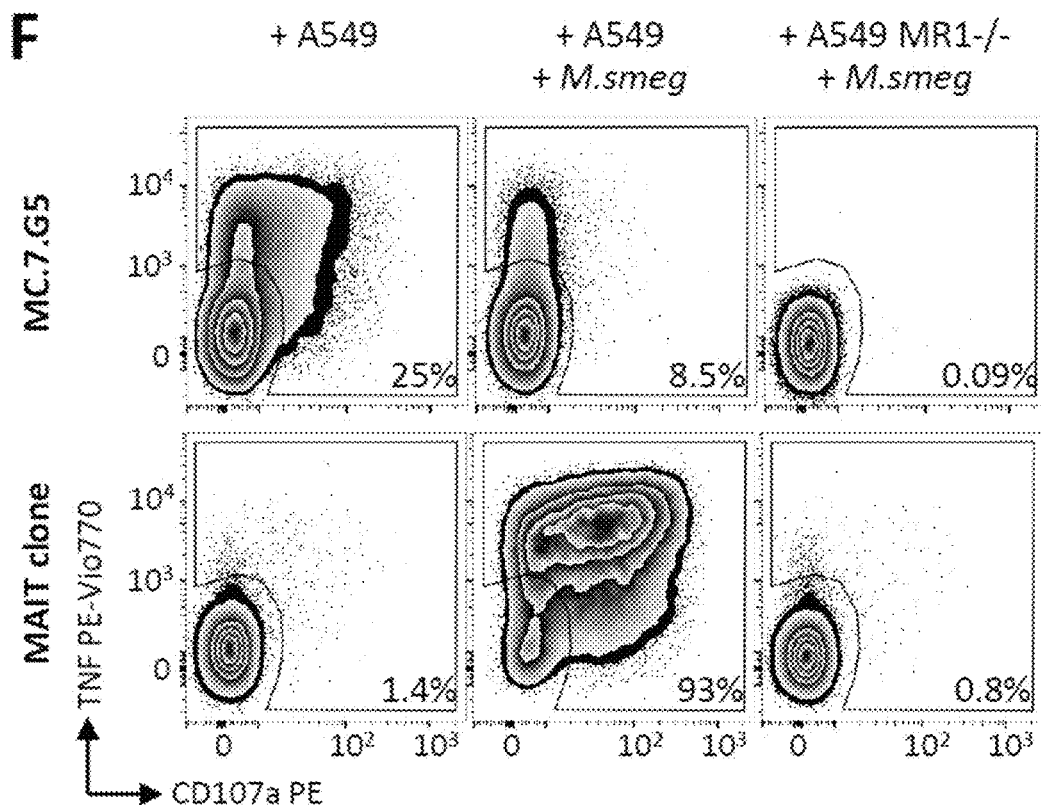
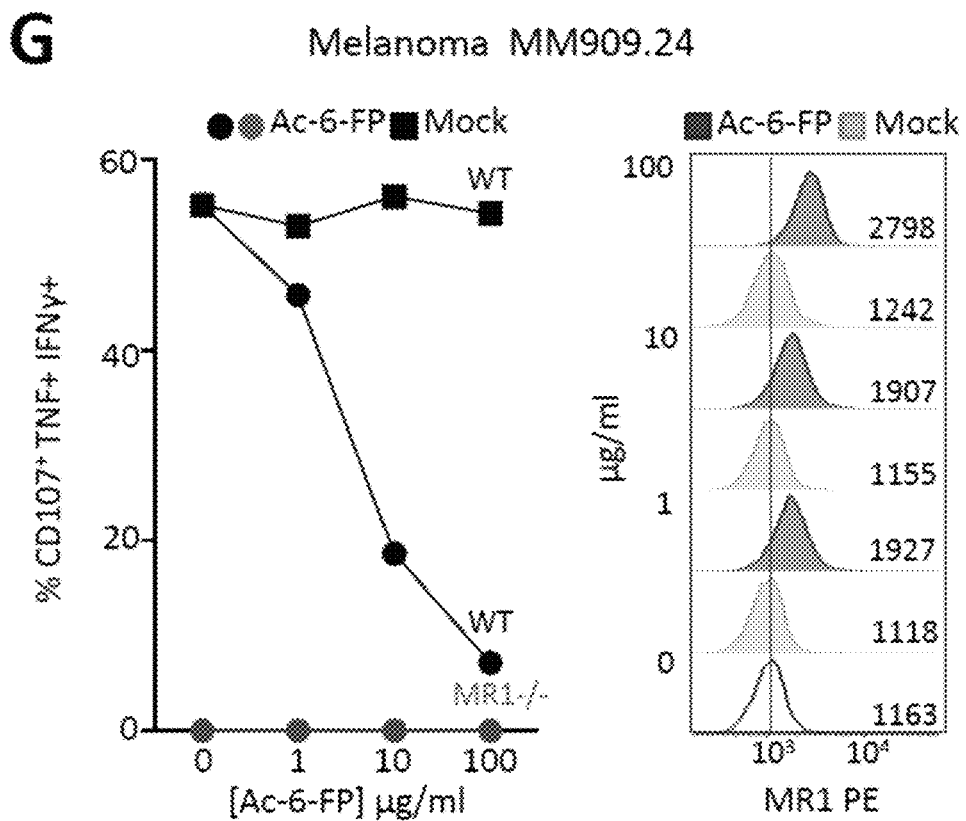
Figure 14 continued

A
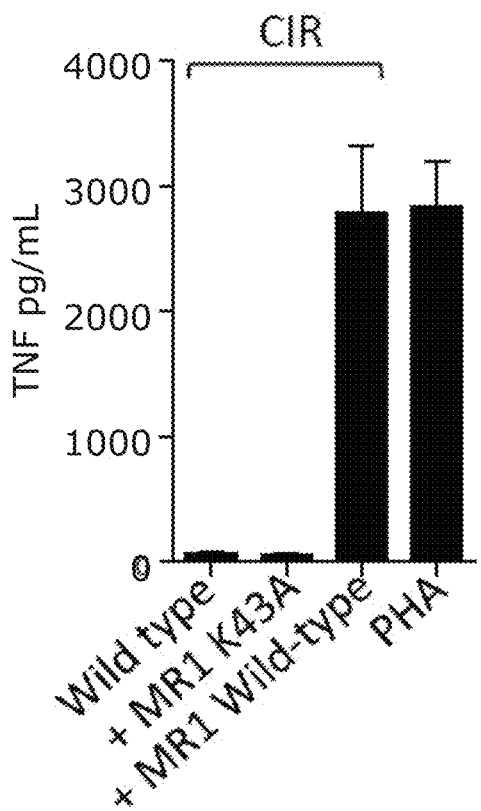
B
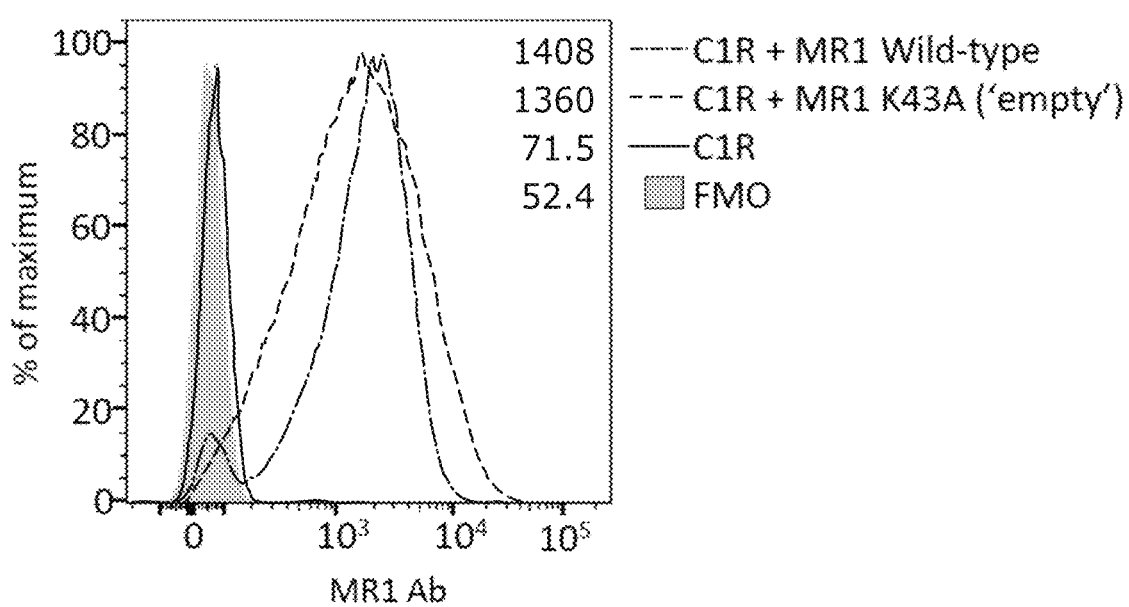
Figure 18

T-CELL RECEPTOR

CROSS REFERENCE

This application is a continuation of U.S. patent application Ser. No. 16/858,082, filed Apr. 24, 2020, which is a continuation-in-part of International Patent Application No. PCT/GB2018/053045, filed Oct. 22, 2018, which claims priority to GB 1717578.7, filed Oct. 26, 2017 and GB 1806155.6, filed Apr. 16, 2018, the contents of each of which are hereby incorporated by reference in their entireties.

SEQUENCE LISTING

The sequence listing filed herewith named "714082_EBW-003PCCIPCON_ST25.txt" (5,653 bytes) was created on Jan. 20, 2021, and is hereby incorporated by reference in its entirety.

TECHNICAL FIELD

The present disclosure relates to a new T-cell receptor (TCR), in particular at least one complementarity-determining region (CDR) thereof; a T-cell expressing said TCR; a clone expressing said TCR; a vector encoding said TCR; a soluble version of said TCR; a pharmaceutical composition or bispecific or vaccine comprising said TCR, said cell, said clone or said vector; use of said TCR or said cell or said clone or said vector or said pharmaceutical composition or immunogenic agent or bispecific or vaccine to treat cancer; and a method of treating cancer using said TCR, said cell, said clone, said vector, said pharmaceutical composition or bispecific comprising said TCR.

BACKGROUND

We have discovered a new class of T-cell effective for treating cancer, which recognize cancer cells through population-invariant major histocompatibility complex class related protein (MR)1. The identification of this new T-cell stemmed from experiments searching for T-cells recognising cancer cells without the requirement for a specific Human Leukocyte Antigen (HLA). The HLA locus is highly variable with over 17,000 different alleles having been described today. As such, any therapeutic approach that works via an HLA can only be effective in a subset of patients. In contrast, the entire human population expresses MR1.

The main type of MR1-restricted T-cells that are known are called mucosal-associated invariant T-cells (MAITs). MAITs are known to recognise intermediates of mycobacterial riboflavin biosynthesis. Recent studies by our own and other laboratories have shown that there are also other types of MR1-restricted T-cells that recognise different MR1-bound ligands. The work described herein shows our new type of T-cells have target specificity via MR1 but the TCR does not bind to MR1 per se or to MR1 loaded with known infectious ligands, rather this T-cell recognises a cancer-specific ligand within the MR1 binding groove; MR1 presents a cancer-specific, or cancer-upregulated, ligand to the TCR.

Our new T-cell clone, MC.7.G5, was discovered during a screen of T-cells from a healthy donor that was HLA mismatched for the adenocarcinoma alveolar basal epithelial cell line, A549 (ATCC® reference CCL-185 for information). The experimental approach involved incubating T-cells with A549 cells then isolating and cloning T-cells that had proliferated in response to the A549 cells. Further investigations showed that the MC.7.G5 T-cell clone was able to recognise and kill cancers cells, including cancer cells from a number of organs and tissue types, thus showing the clone had potential for treating many types of cancer.

As is known, and as shown in FIG. 12, the TCR is a disulfide-linked membrane-anchored heterodimeric protein normally consisting of the highly variable alpha (a) and beta (13) chains that associate with the invariant CD3 chain molecules to form a complete functioning TCR. T cells expressing this receptor are referred to as α:β (or αβ) T cells.

The α and beta β chains are composed of extracellular domains comprising a Constant (C) region and a Variable (V) region. The Constant region is proximal to the cell membrane, followed by a transmembrane region and a short cytoplasmic tail, while the Variable region binds to the ligand. The ligand for most αβ T cells is a peptide bound to an HLA molecule.

The variable domain of both the TCR α-chain and β-chain each have three variable regions called complementarity determining regions (CDRs). There is also an additional area of variability on the β-chain (HV4) that does not normally contact antigen and, therefore, is not considered a CDR. In general, the antigen-binding site is formed by the CDR loops of the TCR α-chain and β-chain. CDR1α and CDR2α are encoded by the individual Vα genes whereas CDR1β and CDR2β are encoded by the individual Vβ genes. The CDR3 of the TCR α-chain is hypervariable due to the potential for nucleotide addition and removal around the joining of the V region and a Joining region. The TCR β-chain CDR3 has even more capacity for variation as it can also include a diversity (D) gene.

CDR3 is the main CDR responsible for recognizing processed antigen, although CDR1 of the alpha chain has also been shown to interact with the N-terminal part of the antigenic peptide, and CDR1 of the β-chain interacts with the C-terminal part of the peptide.

In 2015 about 90.5 million people had cancer. About 14.1 million new cases occur a year (not including skin cancer other than melanoma). It causes about 8.8 million deaths (15.7%) of human deaths. The most common types of cancer in males are lung cancer, prostate cancer, colorectal cancer and stomach cancer. In females, the most common types of cancer are breast cancer, colorectal cancer, lung cancer and cervical cancer. If skin cancer, other than melanoma, were included in total new cancers each year it would account for around 40% of cases. In children, acute lymphoblastic leukaemia and brain tumours are most common except in Africa where non-Hodgkin lymphoma occurs more often. In 2012, about 165,000 children under 15 years of age were diagnosed with cancer. The risk of cancer increases significantly with age and many cancers occur more commonly in developed countries. Rates are increasing as more people live to an old age and as lifestyle changes occur in the developing world. The financial costs of cancer were estimated at $1.16 trillion USD per year as of 2010. It follows that there is a need to provide better and safer ways of treating or eradicating this disease. An immunotherapy that uses the body's natural defence systems to kill aberrant tissue is acknowledged to be safer than chemical intervention but, to be effective, the immunotherapy must be cancer specific. Moreover, the discovery of an immunotherapy that is effective against any type of cancer would be extremely beneficial as not only could it be administered to individuals suffering from many different types of cancer (i.e. it would have pan-population application) but it could also be administered to a single individual suffering from more than one type of cancer. Additionally, the identification of an immunotherapy that was not-restricted would also be extremely advantageous as it means it could be administered to any individual regardless of MHC tissue type.

The T-cells we have identified herein have the afore advantageous characteristics in that they are effective against any type of cancer and they are not MHC-restricted and so have pan-population application due to the ubiquitous expression of the restricting MR1 molecule.

STATEMENTS OF INVENTION

According to a first aspect of the invention there is provided a tumour-specific T-cell receptor (TCR) characterised by a comprising or consisting of CAYRSAVNARLMF (SEQ ID NO: 1) and/or CASSEARGLAEFTDTQYF (SEQ ID No: 2).

In a preferred embodiment of the invention said CDR comprises or consists of (CDR) CAYRSAVNARLMF (SEQ ID NO: 1) and/or CASSEARGLAEFTDTQYF (SEQ ID No: 2) or a CDR that shares at least 88% identity therewith, such as 89%, 90%, 91%, 92%, 93%, 94%, 95%, 96%, 97%, 98% or 99%.

The CDRs described herein represent the CDR3s of said TCR are the main CDRs responsible for recognizing processed antigen or ligand. The other CDRs (CDR1alpha, CDR2alpha, CDR1beta and CDR2beta are encoded by the germline. Therefore, the invention further concerns a TCR also including one or more of these other CDRs i.e. CDR1alpha, CDR2alpha, CDR1beta or CDR2beta.

Accordingly, in a preferred embodiment said TCR comprises one or more, including any combination, of the following complementarity-determining regions:

(CDR1α)
TSESDYY        SEQ ID NO: 3

(CDR2α)
ATEN           SEQ ID NO: 4

(CDR1β)
MGHDK          SEQ ID NO: 5

(CDR2β)
SYGVNS         SEQ ID NO: 6

Reference herein to a specific TCR is to a TCR that specifically recognises a tumour cell or a tumour cell ligand, in the context of MR1, and is activated by same but is not activated by a non-tumour cell or a non-tumour cell ligand, in the context of MR1.

In a preferred embodiment of the invention said TCR is an αβ TCR having an α chain and a β chain and said CDR of said α chain comprises or consists of the CDR: CAYRSAVNARLMF (SEQ ID NO: 1) or a CDR that shares at least 88% identity therewith, such as 89%, 90%, 91%, 92%, 93%, 94%, 95%, 96%, 97%, 98% or 99%; and said CDR of said β chain comprises or consists of the CDR: CASSEARGLAEFTDTQYF (SEQ ID No: 2) or a CDR that shares at least 88% identity therewith, such as 89%, 90%, 91%, 92%, 93%, 94%, 95%, 96%, 97%, 98% or 99%. Accordingly, said TCR may comprise one or both of the afore CDRs and in a preferred embodiment comprises both of said CDRs.

In yet a further preferred embodiment said TCR is unconventional in that it is not-restricted, rather it binds to a specific ligand in the context of MR1, an alternative MHC-molecule. Hitherto, it was thought that MR1-restricted αβ T-cells were exclusively mucosal-associated invariant T cells (MAIT cells), however, we demonstrate herein that a further class of MR1-restricted T-cells exist that do not express the MAIT TCR α chain, moreover, advantageously, these T-cells and their TCRs are tumour specific (i.e. respond to tumour cells but not no-tumour cells) but, surprisingly, are able to identify any tumour origin or tissue type and so have pan-cancer therapy potential. Further, the fact that these T-cells and their TCRs are not MHC-restricted means they have pan-population therapy potential and so represent an extremely important new cancer therapy.

In a further preferred embodiment of the invention said TCR α chain comprises or consists of:

(SEQ ID NO: 7)
AQTVTQSQPEMSVQEAETVTLSCTYDTSESDYYLFWYKQPPSRQMILVIRQ

EAYKQQNATENRFSVNFQKAAKSFSLKISDSQLGDAAMYFCAYRSAVNARL

MFGDGTQLVVKPNIQNPDPAVYQLRDSKSSDKSVCLFTDFDSQTNVSQSKD

SDVYITDKC̲V̲LDMRSMDFKSNSAVAWSNKSDFACANAFNNSIIPEDTFFPS

PESS or a sequence that has at least 88% identity therewith, such as 89%, 90%, 91%, 92%, 93%, 94%, 95%, 96%, 97%, 98% or 99%.

In a further preferred embodiment of the invention said TCR β chain comprises or consists of:

(SEQ ID NO: 8)
EADIYQTPRYLVIGTGKKITLECSQTMGHDKMYWYQQDPGMELHLIHYSYG

VNSTEKGDLSSESTVSRIRTEHFPLTLESARPSHTSQYLCASSEARGLAEF

TDTQYFGPGTRLTVLEDLKNVFPPEVAVFEPSEAEISHTQKATLVCLATGF

YPDHVELSWWVNGKEVHSGVCTDPQPLKEQPALNDSRYALSSRLRVSATFW

QDPRNHFRCQVQFYGLSENDEWTQDRAKPVTQIVSAEAWGRAD or a sequence that has at least 88% identity therewith, such as 89%, 90%, 91%, 92%, 93%, 94%, 95%, 96%, 97%, 98% or 99%.

(In the above paragraphs, the bold and underlined text represents the CDRs)

In yet a further preferred embodiment of the invention said TCR comprises said afore TCR α chain and said afore TCR β chain.

In yet a further preferred embodiment, said TCR is a soluble TCR, or sTCR, and so lacks the transmembrane and, ideally also, intracellular domains.

In yet another preferred embodiment of the invention said TCR is part of a chimeric receptor having the functionality described herein.

According to a further aspect of the invention there is provided a T-cell expressing said TCR of the invention, ideally, in either a soluble or membrane compatible form i.e. having a transmembrane region and intracellular region.

According to a yet further aspect of the invention there is provided a T-cell clone expressing said TCR of the invention, ideally, in either a soluble or membrane compatible form i.e. having a transmembrane region and intracellular region. Preferably said clone is a MC.7.G5 clone as described herein.

According to a yet further aspect of the invention there is provided a vector encoding said TCR of the invention.

According to a yet further aspect of the invention there is provided a pharmaceutical composition or immunogenic agent or bispecific or vaccine comprising said TCR or cell or clone or vector.

In a preferred embodiment said pharmaceutical composition or bispecific is used to treat cancer, particularly colorectal, lung, kidney, prostate, bladder, cervical, melanoma (skin), bone, breast, ovarian or blood cancer.

According to a yet further aspect of the invention there is provided the use of said TCR or cell or clone or vector to treat cancer.

According to a yet further aspect of the invention there is provided a method of treating cancer comprising administering said TCR or cell or clone or vector to an individual to be treated.

Ideally said cancer is of any type but in particular colorectal cancer, lung, kidney, prostrate, bladder, cervical, melanoma (skin), bone, breast, ovarian or blood cancer.

In a preferred method of the invention said TCR, cell, clone or vector is administered in combination with an anti-tumour agent such as, but not limited to, a bispecific.

Reference herein to a bispecific is reference to a bispecific monoclonal antibody (BsMAb, BsAb) which is an artificial protein that can simultaneously bind to two different types of antigen.

Alternatively still, said TCR may form part of a Bispecific wherein said bispecific includes said TCR, for the purpose of binding to its ligand on a cancer cell, and also an immune cell activating component or ligand that binds and so activates an immune cell such as a Killer T-cell.

According to a yet further aspect of the invention there is provided the use of said TCR or cell or clone or vector in the manufacture of a medicament to treat cancer.

According to a yet further aspect of the invention there is provided a combination therapeutic for the treatment of cancer comprising:
a) said TCR or cell or clone or vector in combination with
b) a further cancer therapeutic agent.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Throughout the description and claims of this specification, the singular encompasses the plural unless the context otherwise requires. In particular, where the indefinite article is used, the specification is to be understood as contemplating plurality as well as singularity, unless the context requires otherwise.

An embodiment of the present invention will now be described by way of example only with reference to the following wherein:

FIG. 1 shows how MC.7.G5 was isolated and its initial characterisation. A. T-cells were labelled with the dye CFSE, and incubated for 2 weeks with A549s. A reduction in CFSE fluorescence represented those T-cells that had proliferated, allowing A549 reactive T-cells to be isolated. B. MC.7.G5 reactivity for A549 cells, based on release of TNFα, was not hindered by blocking antibodies for MHC class I or II. Supernatants from assays were harvested for analysis by TNFα ELISA. C. Antibody phenotyping panel of MC.7.G5 clone showed it to be γδ− αβ+ CD8+ (repeated in FIG. 16A).

FIG. 2 shows that MC.7.G5 does not respond to normal (non-cancer) cells. Experiment compares TNFα release from clone MC.7.G5 in response to melanoma cell line MM909.24 (cancer target of MC.7.G5) and four primary (non-tumour, non-immortal) cell lines. SMC3 is a smooth muscle cell line; CIL-1 is a ciliated epithelial cell, MCR5 is an hTERT transduced fibroblast cell line; Hep2 is a hepatocyte cell line. (normal cell lines also tested in FIGS. 15 and 17).

FIG. 3 shows the sequence of the MC.7.G5 TCR α and β chains.

FIG. 4 shows Clone MC.7.G5 responds to a wide range of tumour targets. Supernatants harvested from T cell activation assay showing MC.7.G5 response to a panel of tumours and examined for TNFα and MIP1β production. B. Chromium Release Assay showing specific killing of cancer cells at the ratios of T-cell to cancer cell shown. A&B Performed in duplicate with error bars.

FIG. 5 shows gene trapping by whole genome CRISPR approach used to identify MR1 as the ligand of clone MC.7.G5. The data for the MC.7.G5 clone CRISPR library screen is shown in FIG. 13.

FIG. 6 shows Clone MC.7.G5 shows target specificity via MR1. A. MR1 antibody blocked recognition of A549 cells. TNFα and MIP1β production by ELISA. B. A549c9 and melanoma MM909.24c4 MR1 knockouts (CRISPR/Cas 9 technology) were not recognised by MC.7.G5. C. There was no specific killing of the MR1 knockout A549c9 cells or the primary cell line MRCS. Killing of MM909.24 wt and A549 wt is also shown. D. Over expression of MR1 in this cell line by lentiviral transduction slightly enhances recognition. LCL line pt146 is not recognised by clone MC.7.G5 even when it is transduced to over-express MR1. Some of this MR1 is presented at the cell surface and can be detected with a MR1 antibody (right).

FIG. 7 shows Clone MC.7.G5 does not stain with tetrameric forms of the MAIT ligand MR1-5-(2-oxopropylideneamino)-6-d-ribitylaminouracil (MR1-5-OP-RU) or with MR1 acetyl-6-formylpterin (Ac-6-FP). In parallel experiments a MAIT clone stained well with MR1-5-OP-RU tetramer. There is also a small population of cells that stain with MR1-5-OP-RU in PBMC population. It is expected that there will be detectable MAIT cells within PBMC samples. This result shows that the MC.7.G5 TCR does not bind to MR1 per se or to MR1 loaded with known infectious ligands and suggest that this T-cell recognises a cancer-specific ligand within the MR1 binding groove. Repeated tetramer staining experiments are shown in FIG. 14E, including those with 'empty' MR1)

FIG. 8 shows Ac-6-FP and *M. smeg* infection reduces recognition by clone MC.7.G5 despite enhancing expression of MR1 at the cell surface. Incubation of A549 or MM909.24 cells with 50 μg/mL of Ac-6-FP for 12 hours increases MR1 expression at the surface but reduces recognition by clone MC.7.G5. The effects of *M. smeg* infection are even more dramatic and substantially reduce the response of clone MC.7.G5 while acting as a potent activator of a MAIT clone. Repeated *M. smeg* and Ac-6-FP experiments are shown in FIG. 14F&G.

FIG. 12 show the Structure of T cell receptor mRNA and Protein. The mRNA structures (top) show that for each chain CDR1 and CDR2 are encoded in the germline. CDR3 is the product of junctional diversity at V-J joins of T cell receptor (TCR)-α chain and V-D-J joins in TCR-β chain. CDR3 is consequently hypervariable. The colour code adopted for the CDR loops is maintained throughout the figure. The areas coloured in grey represent the constant and variable domains of the TCRs (not including the hypervariable CDR loops). The bottom panel shows the expected protein fold. TCRs adopt similar tertiary structures that position the complementarity-determining regions (CDR) loops at the membrane distal end of the molecules. Together the six CDR loops form the antigen binding site.

Figure 13:
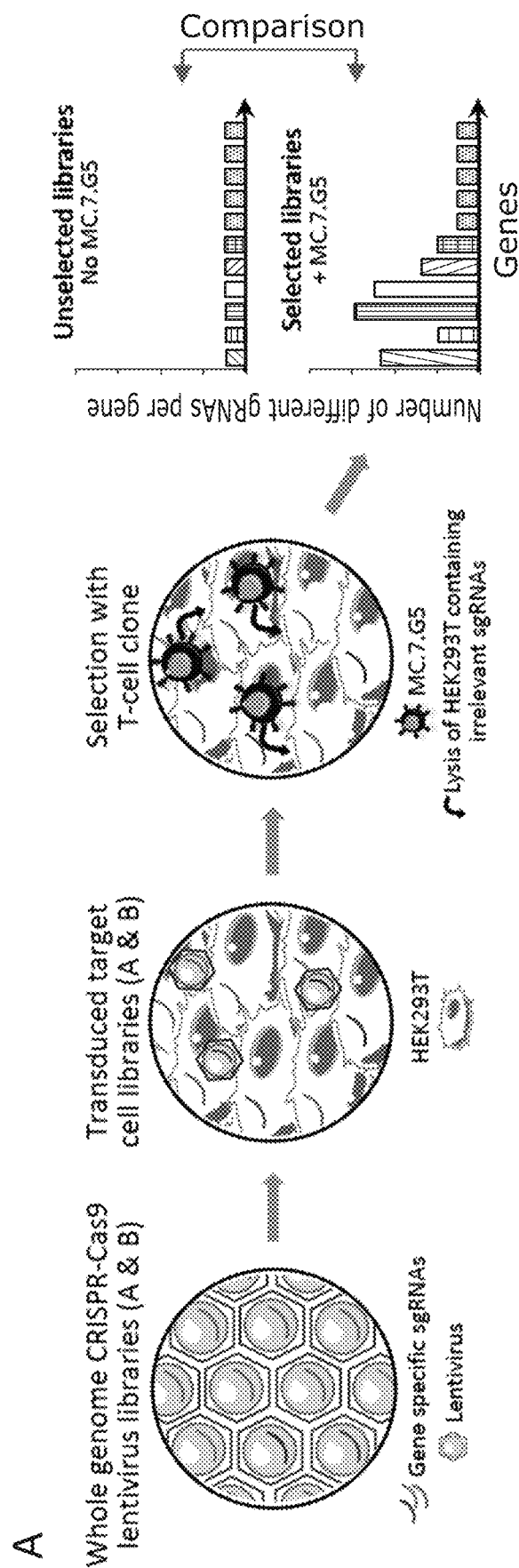
Figure 13:
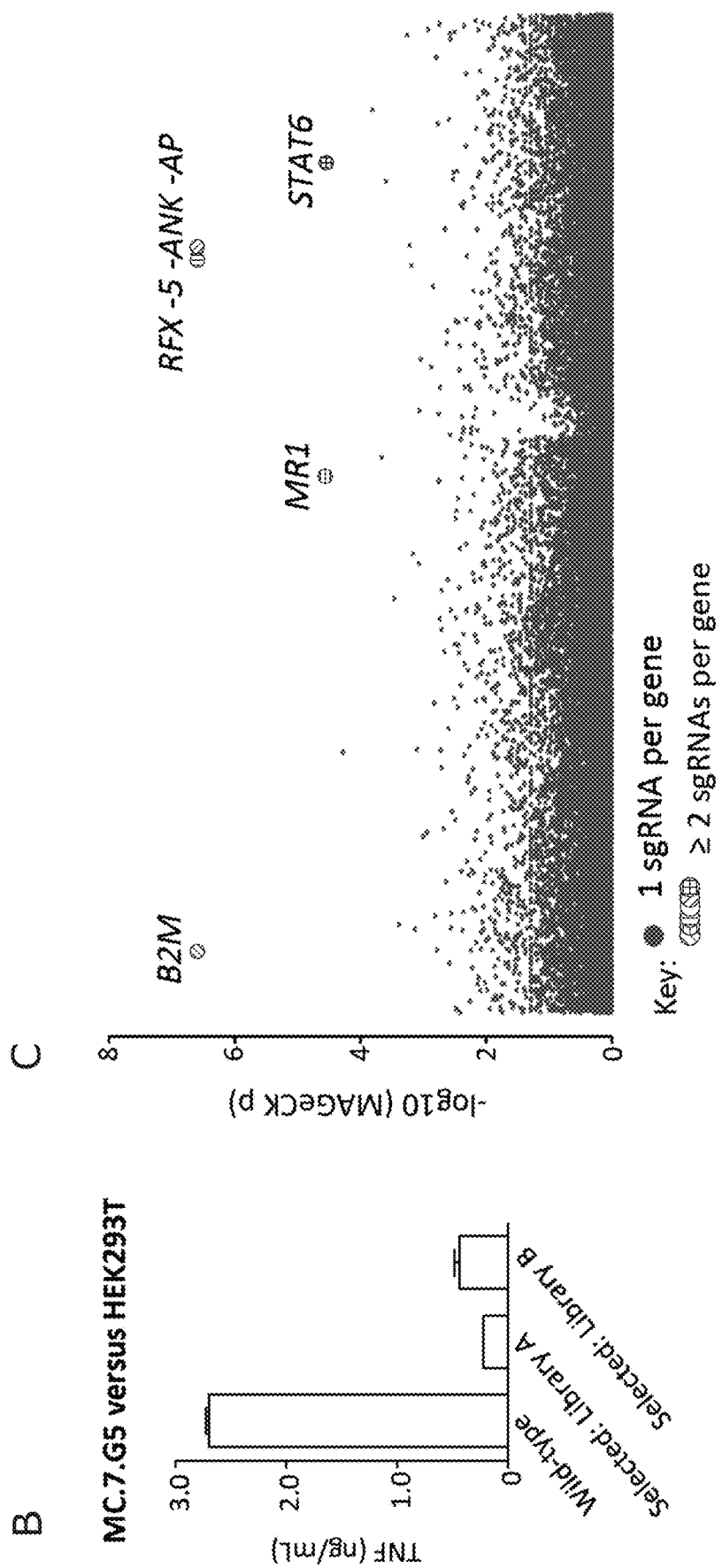

FIG. 13. Whole genome CRISPR-Cas9 library screening reveals MR1 as the candidate target of MC.7.G5. (A) Overview of the approach used to reveal the ligand of MC.7.G5. GeCKO v2 whole genome CRISPR/Cas9 libraries A and B were used as lentivirus to transduce target cell line HEK293T. MC.7.G5 lysed HEK293T expressing sgRNAs for genes that are irrelevant for HEK293T recognition, thereby enriching sgRNAs for genes that are essential for cancer cell lysis by MC.7.G5. Two rounds of selection with MC.7.G5 were performed and the selected libraries compared to unselected HEK293T (no MC.7.G5) to reveal enriched sgRNAs. (B) MC.7.G5 recognition of selected HEK293T library post-selection is greatly reduced compared to wild-type HEK293T, suggesting key genes had been ablated by the whole genome CRISPR-Cas9 approach. Overnight activation and TNF ELISA. (C) MR1 was identified as one of key genes for MC.7.G5 recognition of HEK293T. MAGeCK analysis and highlighted (coloured) genes with sgRNAs enriched in the selected HEK293T cells. Validation of MR1 as the target of MC.7.G5 is shown in FIG. 14.

Figure 14:
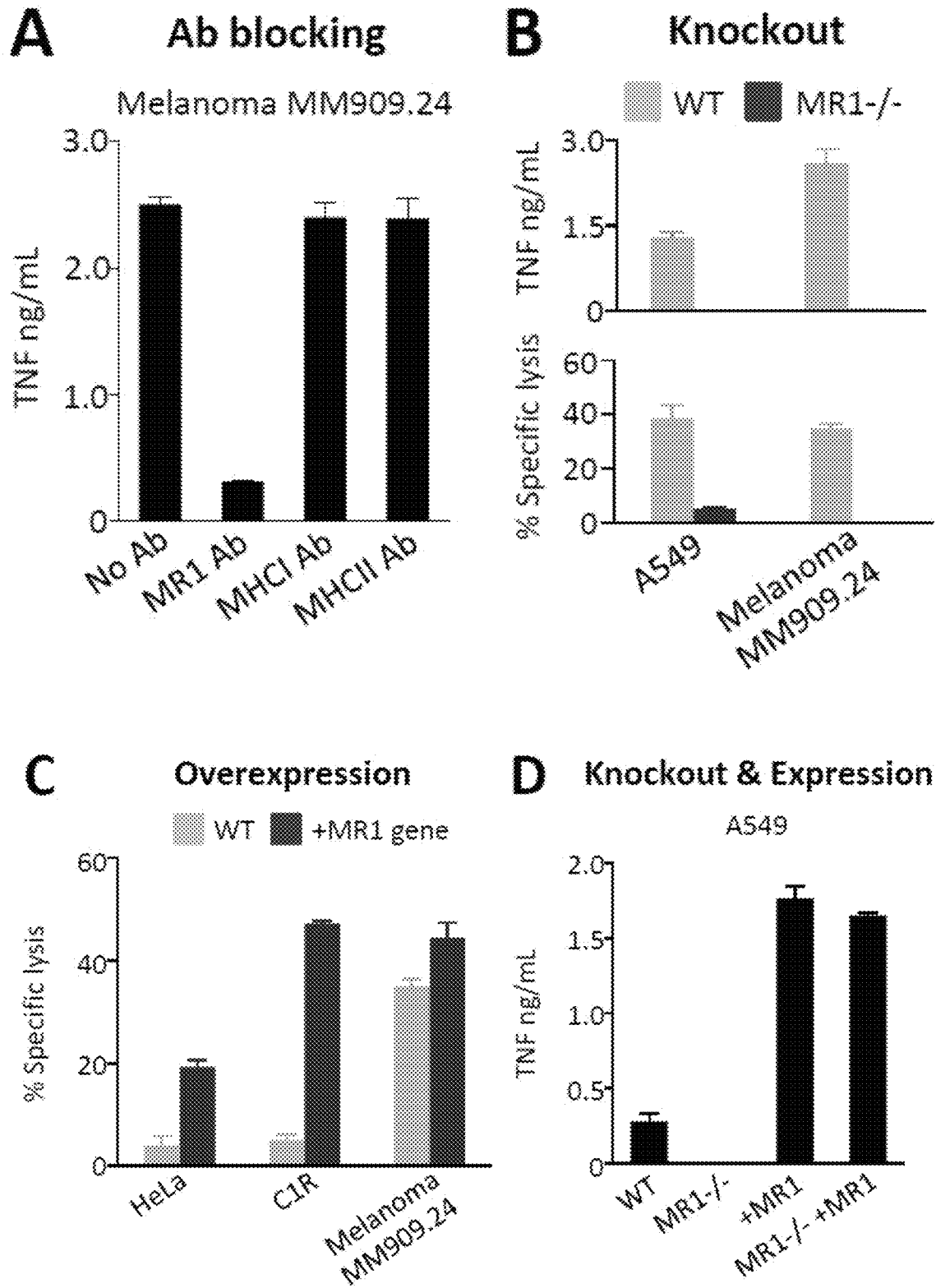
Figure 14:
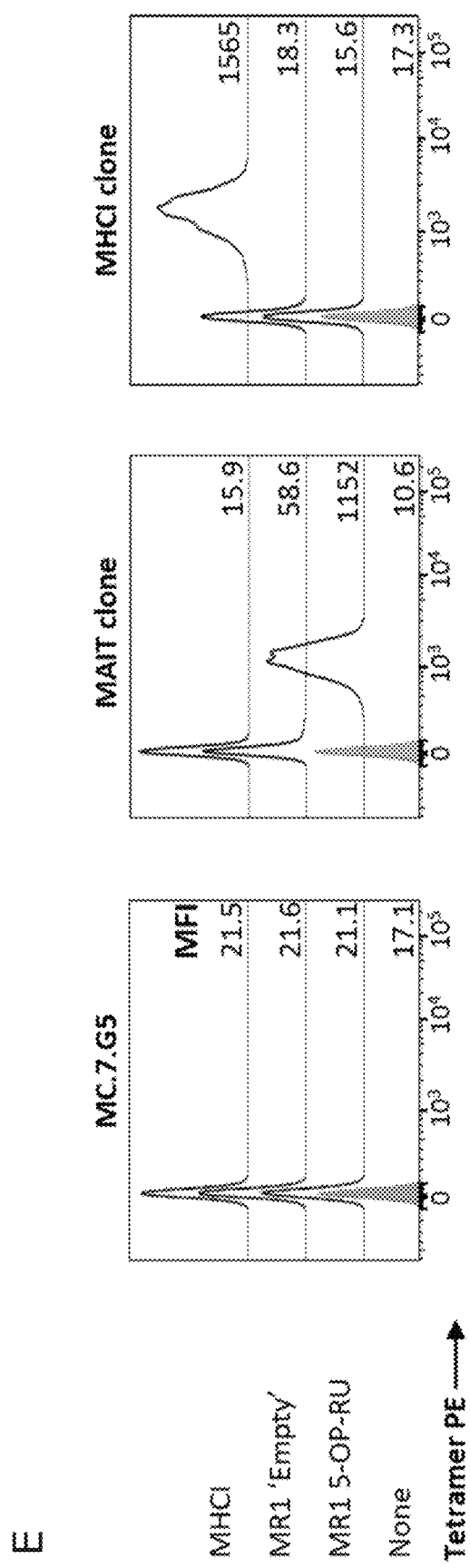

FIG. 14. Validation and exploration of MR1 recognition by MC.7.G5. (A-D) MR1 is the cancer cell expressed target of MC.7.G5. (A) Recognition of melanoma MM909.24 was reduced in the presence of MR1 blocking antibody (Ab). MHCI and II Abs were used as negative control. Overnight activation and TNF ELISA. (B) Removal of MR1 expression from cancer cell lines prevented MC.7.G5 mediated recognition and killing. Melanoma MM909.24 and lung adenocarcinoma A549s were transduced with a sg RNA to knockout (−/−) the MR1 gene via CRIPSRCas9. Overnight activation and TNF ELISA. Chromium release cytotoxicity assay for 6 h (MM909.24) or 18 h (A549). (C) Overexpression (+) of MR1 improved cancer cell killing by MC.7.G5. Cancer cell lines C1R and HeLa that had been shown to induce relatively low MC.7.G5 activation were lentivirally transduced to stably overexpress MR1. Melanoma MM909.24 was included as a positive control. Chromium release cytotoxicity assay performed for 6 h. (D) Expression of MR1 in MR1−/− cells restores activation of MC.7.G5. A549 wildtype, MR1−/− and MR1−/− cells with a MR1 transgene (+) were used in an overnight activation assay with MC.7.G5. TNF ELISA. (E&F) MC.7.G5 does not recognise MR1 by known mechanisms: (E) MC.7.G5 clone, a canonical MAIT clone (recognizes MR1 with bound 5-OP-RU), and an MHCI restricted clone (MELS/13, HLA A2 restricted, Melan A peptide ELAGIGILTV) were used for staining with the following tetramers: MR1 'Empty' (K43A mutant to enable refolding in the absence of a MR1 ligand), MR1 5-OP-RU and MHCI (HLA A2 ELAGIGILTV). The MHCI clone was used as a positive control for the irrelevant MHCI tetramer. (F) A549s loaded with MAIT-activating bacterium *Mycobacterium smegmatis* reduced MC.7.G5 recognition of A549. The canonical MAIT clone from E was used as a positive control. A549 MR1−/− was used as a negative control for both clones. Staining for surface CD107a and intracellular TNF. Gate set on clone alone. (G) Exogenous Ac-6-FP, a known MR1 binding molecule, reduced MC.7.G5 recognition of melanoma MM909.24. Mock treated WT and Ac-6-FP MR1−/− targets used as controls. Left panel: Staining for intracellular CD107a, TNF and IFNγ with triple positivity analysed by FlowJo. Error bars smaller than plot symbols, representative of two experiments. Right panel: MR1 expression on Ac-6-FP treated target cells.

Figure 15:
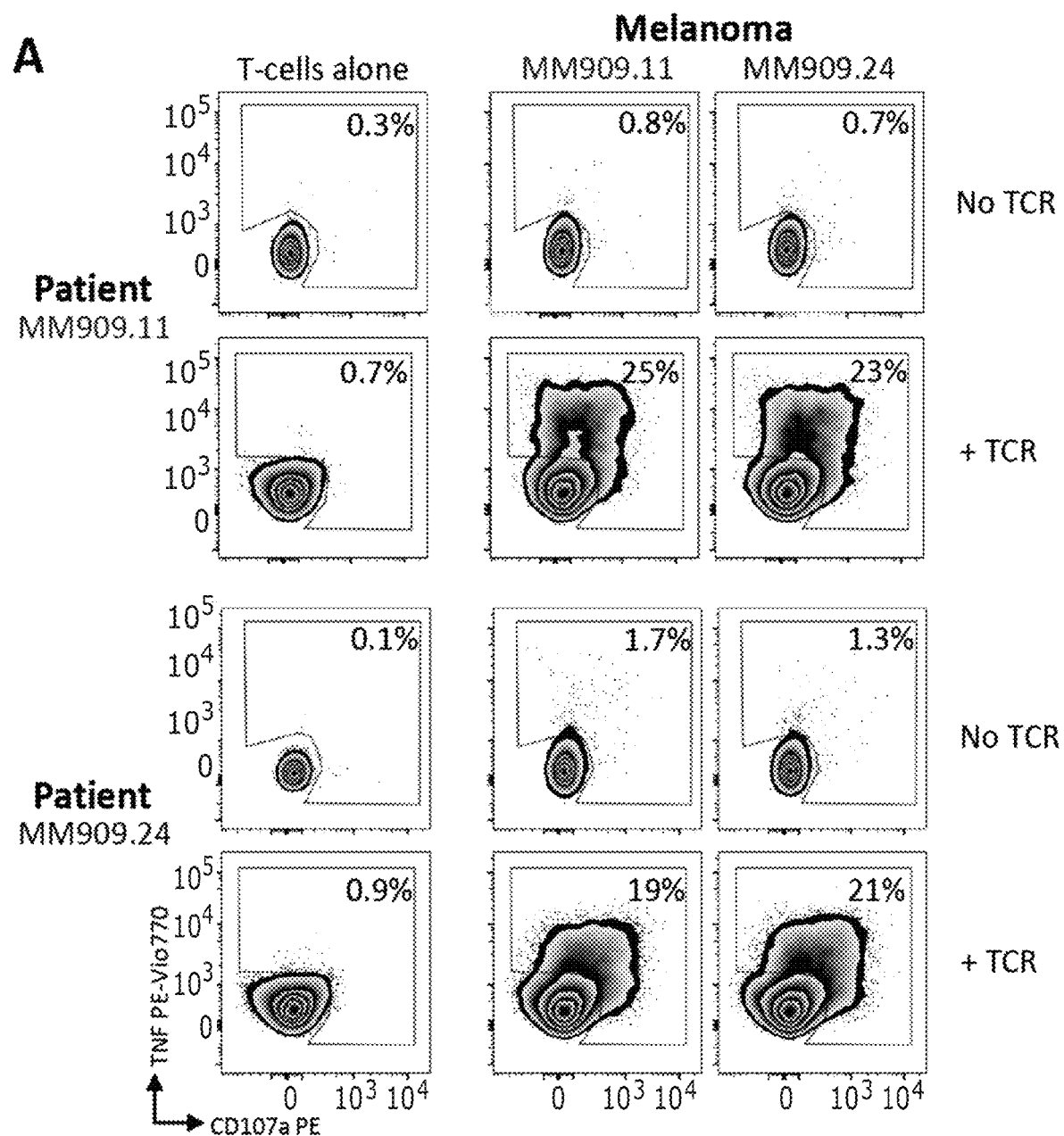
Figure 15:
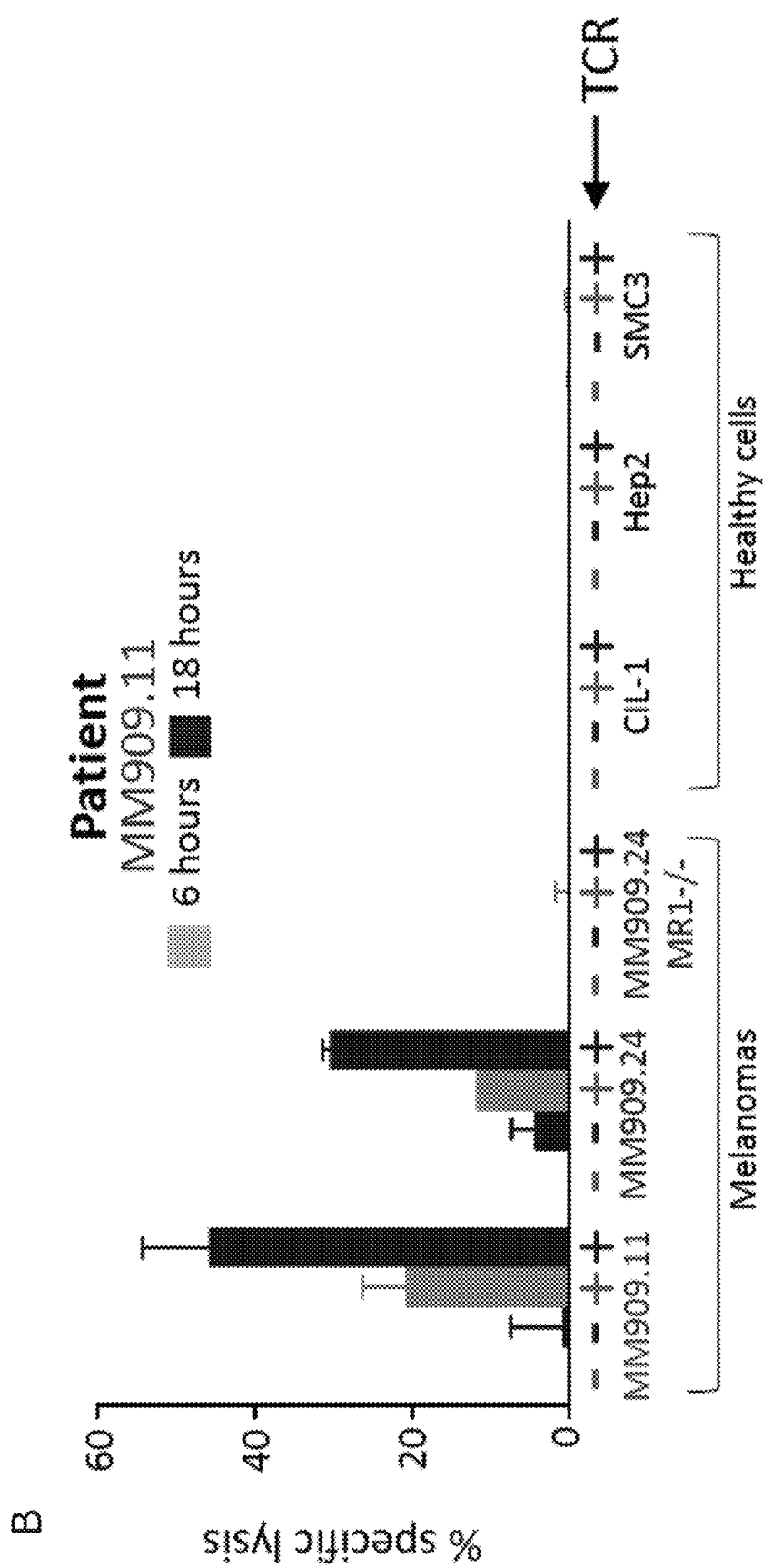

FIG. 15. Transfer of the MC.7.G5 T-cell receptor redirects patient T-cells to kill autologous melanoma. (A) Metastatic melanoma patient (MM909.11 and MM909.24) derived T-cells transduced with the T-cell receptor of MC.7.G5 recognised autologous and non-autologous melanomas. Untransduced T-cells were used as a negative control. Staining for surface CD107a and intracellular TNF following 4 h of activation. (B) T-cells from patient MM909.11 transduced with MC.7.G5 TCR killed autologous and nonautologous melanomas, but not healthy cells. Chromium release cytotoxicity assay with untransduced (−) and MC.7.G5 TCR transduced (+) T-cells from patient MM909.11 versus autologous melanoma, melanoma from patient MM909.24 (wildtype and MR1 knockout (−/−)) and healthy cell lines: SMC3 (smooth muscle); CIL-1 (ciliated epithelial); and Hep2 (hepatocyte). Performed at a T-cell to target cell ratio of 5:1, for 6 h and 18 h.

Figure 16:
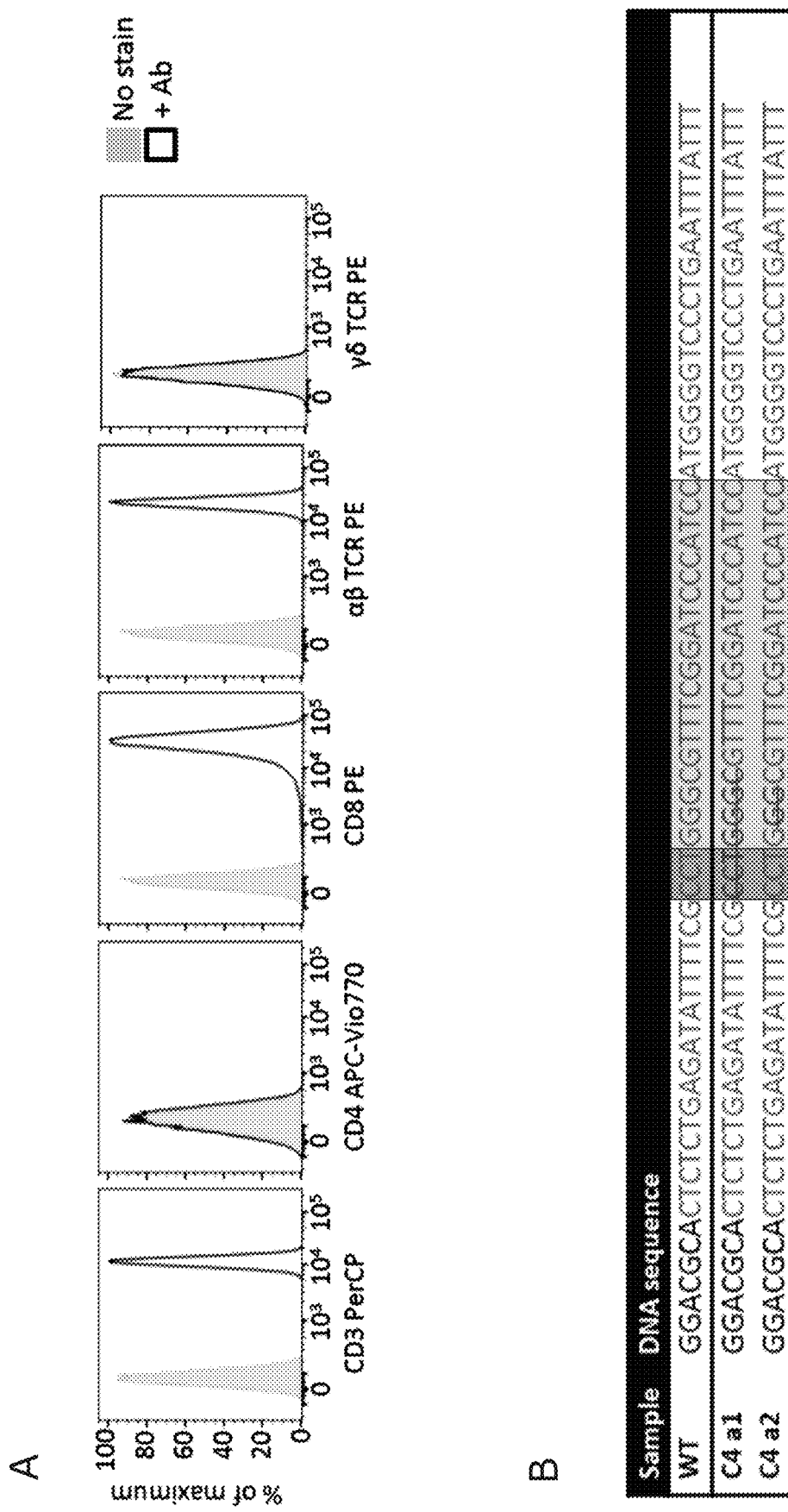
Figure 16:
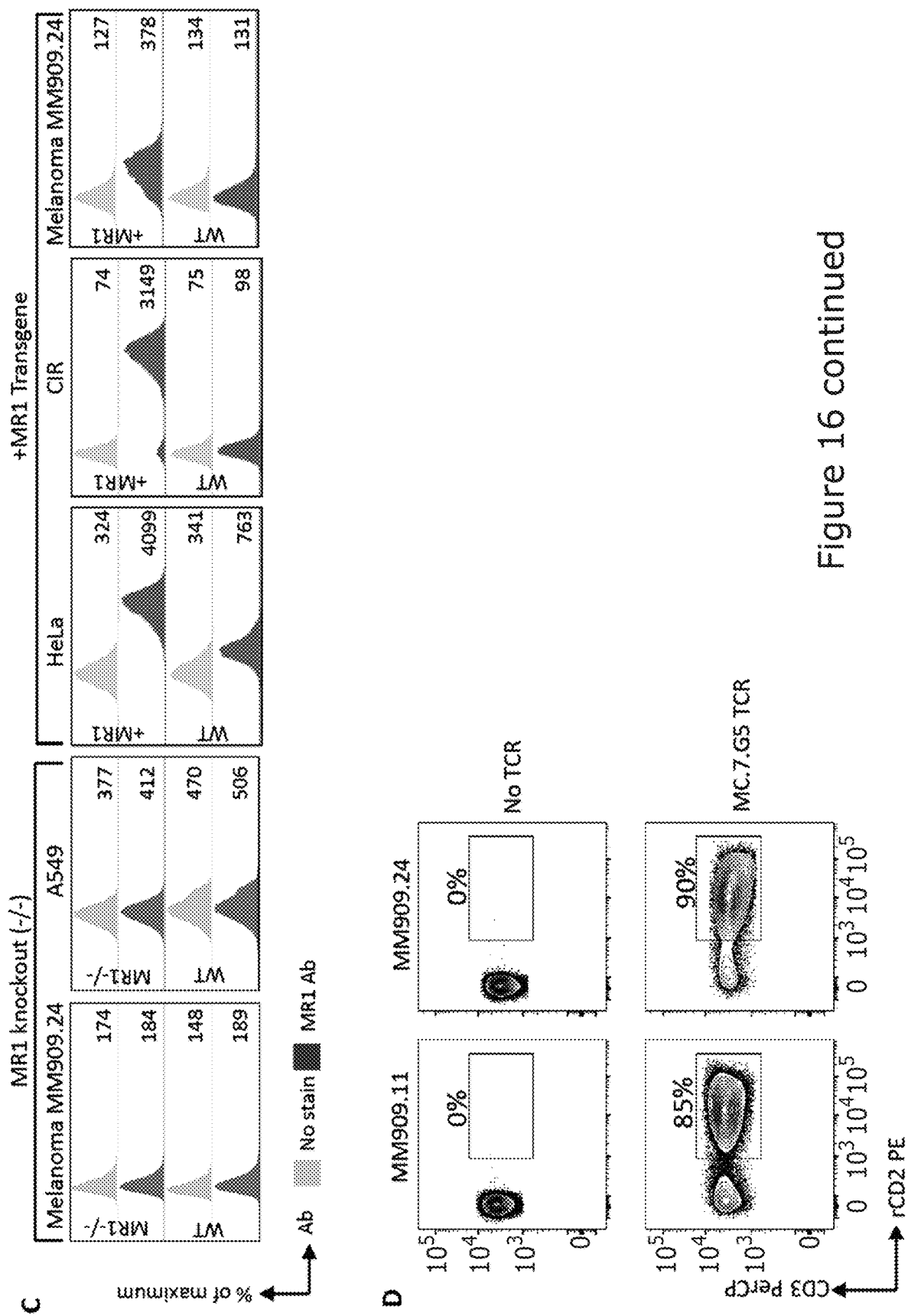

FIG. 16. (A) Phenotyping by flow cytometry of MC.7.G5. (B) Genomic sequence of the MR1 locus of melanoma MM909.24 with MR1 CRISPR-Cas9 induced biallelic deletion in exon 2. (C) MR1 expression of the target cells used in FIG. 14A-D assessed with an anti-MR1 antibody (Ab). (D) rCD2 staining of T-cells from melanoma patients MM909.11 and MM909.24, with and without transduced MC.7.G5 TCR.

Figure 4:
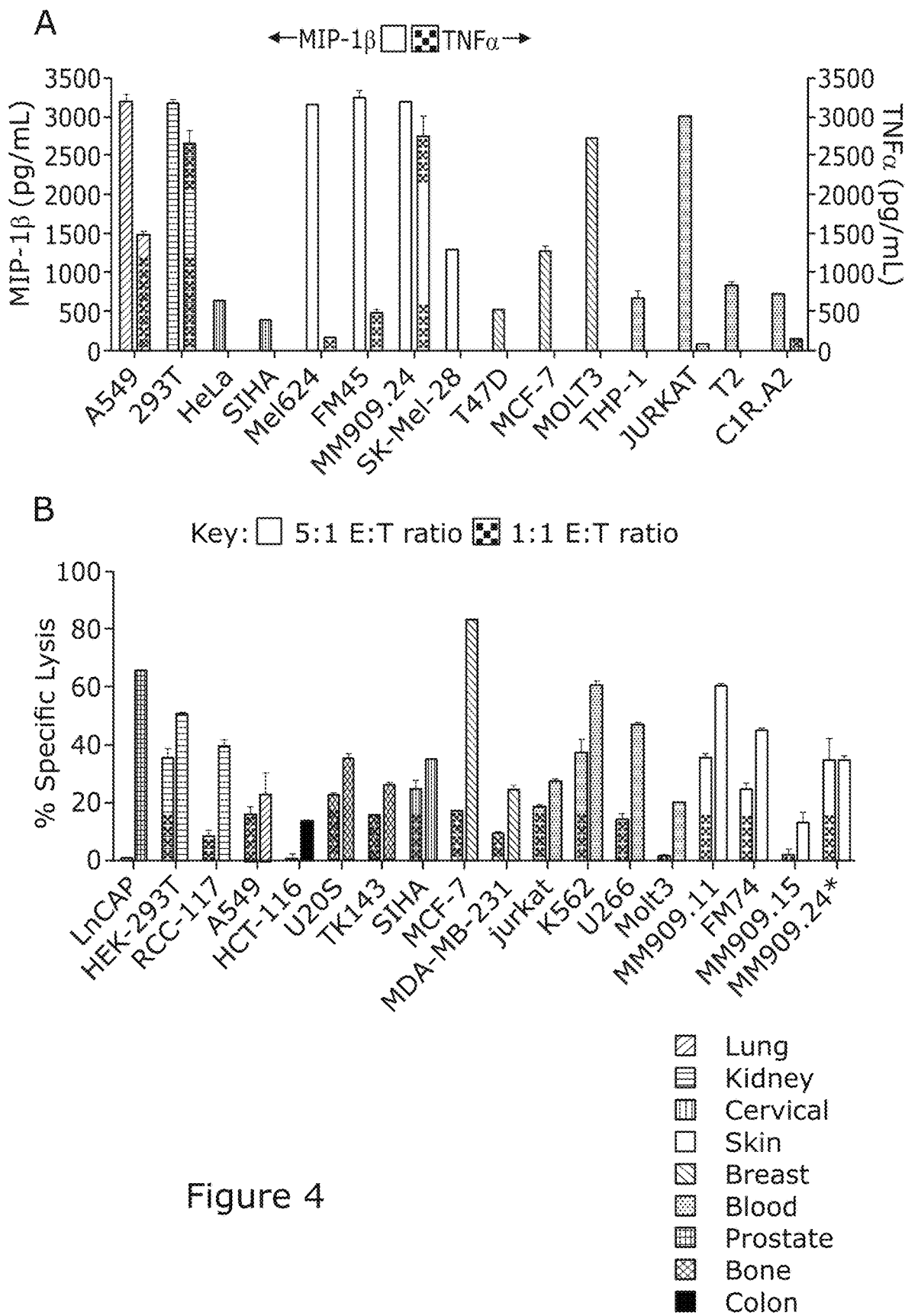
Figure 17:
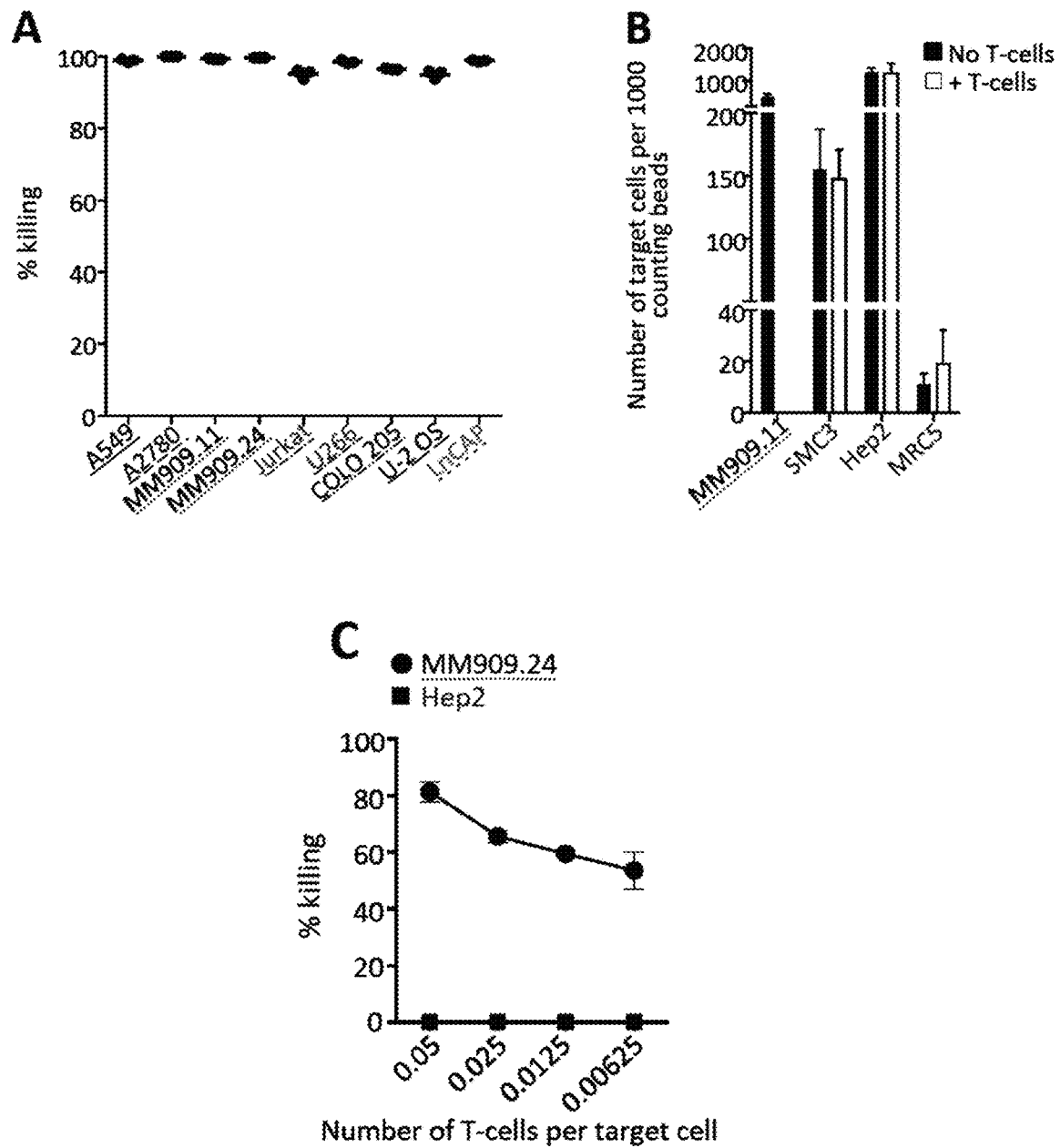

FIG. 17. MC.7.G5 killing of a range of cancer cell lines (x-axis) of different origin (key) after 48 hours of co-incubation ('long-term killing assay') (A). This shows that MC.7.G5 was capable of killing 95-99.9% of each cell line thereby supplementing the data from relatively shorter-term killing assays shown in FIG. 4. Incubated at a T-cell to target cell ratio of 5:1 and extent of killing determined using counting beads or CFSE labelled reference cells. (B) MC.7.G5 did not kill normal cells when co-incubated for 7 days. T-cell to target cell ratio of 5:1 and counting beads used to establish the number of target cells that remained. SMC3 (smooth muscle), Hep2 (hepatocyte) and MRCS (skin fibroblast). Melanoma MM909.11 was used as a positive control. Displayed as the number of target cells (healthy or melanoma) per 1000 counting beads±MC.7.G5. (C) MC.7.G5 sensitively killed melanoma MM909.24. Incubated for 7 days and CFSE labelled reference cells used to establish the extent of killing. In the same assay normal cell line Hep2 was not killed.

FIG. 18 shows that overexpression of mutated K43A ('empty') MR1 in C[I]]1Rs cells did not lead to activation of M.7.G5 (A) despite high staining of the C[I]1 Rs-K43A with MR1 antibody (B). In contrast, overexpression of wild-type MR1 in C[I]1 Rs induced MC.7.G5 activation. This further demonstrates that the MC.7.G5 TCR recognizes MR1 with a bound cargo and reinforces the data in FIG. 14E showing no staining of MC.7.G5 with empty K43A MR1 tetramer.

DETAILED DESCRIPTION

Methods and Materials
Procurement and Characterisation of T-Cell Clone MC.7.G5.

Peripheral blood mononuclear cells (PBMCs) were purified from the blood of a healthy donor by standard density gradient separation, then stimulated with the human adenocarcinoma alveolar basal epithelial cell line, A549 (ATCC® CCL-185 for culture conditions and background information). In order to track T-cell proliferation in response to A549s the PBMCs were labelled with the cell dye Carboxyfluorescein succinimydl ester (CFSE, Molecular Probes, Thermo Fisher Scientific, Waltham, Mass.). PBMCs were washed extensively in PBS then incubated at 37° C. for 10 min in the dark with 1 µM CFSE, followed by quenching with an excess of foetal bovine serum. The CFSE labelled PBMCs were cultured alone, or with the A549s in 24 well tissue culture plates at a density of 6-8×10$^6$ PBMC and 0.1-0.2×10$^6$ A549 in T-cell priming media (Theaker et al., 2016). Culture media was changed (50% by volume) three times weekly and the cells incubated for a total of 2 weeks. To assess the degree of proliferation in response to A549s the cells were harvested from culture washed in PBS and labelled with the cell viability dye Vivid (1:40 dilution in PBS then 2 µL per stain in 50 µL) (Life Technologies) and incubated at RT for 5 min before the addition of anti-CD3 antibody (Ab) (BW264/56, Miltenyi Biotec, Bergish Gladbach, Germany) for a further 20 min on ice. Cells were gated on lymphocytes (forward versus side scatter), single (forward versus side scatter), and Vivid$^-$CD3$^+$ cells, and for analysis bivariate plots displayed as CD3 Ab versus CFSE. The CFSE$^{low}$ cells (proliferated T-cells) were sorted using a BD FACS Aria (Central Biotechnology Services, Cardiff University, UK) for cloning by limiting dilution as previously described (Theaker et al., 2016). Prior to performing activation assays, MC.7.G5 was harvested, washed and incubated for 24 h in reduced serum medium as described previously (Wooldridge et al., 2012). Subsequently, MC.7G.5 (30,000 per well of a 96 U well plate) was incubated with A549s (60,000 per well) that had been either been left unlabelled, or labelled with 10 µg/mL of MHC class I (W6/32, BioLegend, San Diego, Calif.) or MHC Class II (Tu39, BioLegend) antibodies (Abs) for 1 h. Without washing MC.7G.5 was added to the wells to a final volume of 100 µL, with the clone also incubated alone or with 10 µg/mL of phytohaemagluttinin (PHA). After overnight incubation, supernatants were harvested and developed by TNFα ELISA (R&D Research, Minneapolis, Minn.). MC.7.G5 was stained with Abs for surface expression of CD3 (Miltenyi Biotec), CD8 (BW135/80, Miltenyi Biotec), CD4 (M-T466, Miltenyi Biotec), γδ TCR (11F2, Miltenyi Biotec) and αβ TCR (BW242/412, Miltenyi Biotec). For staining, the clone was harvested from culture, washed with PBS and labelled with the viability stain Vivid at room temperature (RT) followed by each of the Abs separately for 20 min of ice. Acquisition was performed on a Becton Dickinson FACS Canto II and data analysed using FlowJo software (Tree Star). Gating on cell size (lymphocyte gate), vivid$^-$ cells and then the cell surface marker of interest displayed as a histogram.

MC.7.G5 does not Respond to Normal Cells.

Healthy cells and their proprietary culture media were obtained from Sciencell (Carlsbad, Calif.) and used as target cells in activation and cytotoxicity assays described elsewhere in the materials and methods section. SMC3 (human colonic smooth muscle), CIL-1 (human non-pigmented ciliary epithelium) and Hep2 (human hepatocyte) were all used at 60,000 cells per well of a 96 U well plate. Additionally, MRC-5 (lung fibroblast, ATCC® reference CCL-171) that expresses hTERT in order to delay senescence was also used in the same assays.

The Sequence of the MC.7.G5 TCR α and β Chains.

RNA was extracted using the RNEasy Micro kit (Qiagen). cDNA was synthesized using the 5'/3' SMARTer kit (Clontech, Paris, France) according to the manufacturer's instructions. The SMARTer approach used a Murine Moloney Leukaemia Virus (MMLV) reverse transcriptase, a 3' oligo-dT primer and a 5' oligonucleotide to generate cDNA templates, which were flanked by a known, universal anchor sequence. PCR was then set up using a single primer pair. A TCR-β constant region-specific reverse primer (C β-R1, 5'-GAGACCCTCAGGCGGCTGCTC-3', SEQ ID NO: 9, Eurofins Genomics, Ebersberg, Germany) and an anchor-specific forward primer (Clontech) were used in the following PCR reaction: 2.5 µL template cDNA, 0.25 µL High Fidelity Phusion Taq polymerase, 10 µL 5× Phusion buffer, 0.5 µL DMSO (all from Thermo Fisher Scientific), 1 µL dNTP (50 mM each, Life Technologies), 1 µL of each primer (10 µM), and nuclease-free water for a final reaction volume of 50 µL. Subsequently, 2.5 µL of the first PCR products were taken out to set up a nested PCR as above, using a nested primer pair (Cβ-R2, 5'-TGTGTGGCCAGGCACACCAGTGTG-3, SEQ ID NO: 10, Eurofins Genomics and anchor-specific primer from Clontech). For both PCR reactions, cycling conditions were as follows: 94° C. for 5 min, 30 cycles of 94° C. for 30 s, 63° C. for 30 s, 72° C. for 90s, and finally 72° C., for 10 min. The final PCR products were loaded on a 1% agarose gel and purified with the QIAEX II gel extraction kit (Qiagen). Purified products were cloned into Zero-Blunt TOPO and transformed into One Shot Chemically Competent *E. coli* cells for standard sequencing (both from Life Technologies). (d) Clone MC.7.G5 Responds to a Wide Range of Tumour Targets.

Activations assays were performed as above and also cytotoxicity assays using either sodium chromate (Chromium$^{51}$) labelled target cells (Ekeruche-Makinde et al., 2012), or a flow cytometry based long-term killing assay (see elsewhere in the materials and methods section). For chromium release assays each cell line was labelled with 30 µCi of Cr$^{51}$ (Perkin Elmer, Waltham, Mass.) per 1×10$^6$ cells and 2000 target cells used per well (96 U well pates) with MC.7.G5 to achieve the desired T-cell to target cell ratios. After overnight incubation the supernatants were harvested, mixed with scintillant and read using a Microbeta counter and specific lysis calculated as previously described (Ekeruche-Makinde et al., 2012). In addition to the A549s HEK293 Ts above, the details of the cancer cell lines used are as follows: cell line name (ATCC® reference or ECACC number for background and culture information)/tissue or organ of origin: HEK293T (Foetal kidney, CRL-1573); LnCaP (CRL-1740)/prostate; SiHa (HTB-35) and HeLa (CCL-2)/cervical; MCF7 (HTB-22), MDA-MB-231 (CRM-HTB-26) and T47D (HTB-133)/breast; TK143 (CRL-8303) and U20S (HTB-96)/bone; HCT-116 (CCL-247)/colon; Jurkat (TIB-152), T2 (0.174xCEM.T2) (CRL-1992), K562 (CCL-243), C[I]1R expressing HLA-A2 (CRL-1193), THP-1 (TIB-202), U266 (TIB-196) and Molts (CRL-1552)/all blood; FM74 (ECACC 13012422), SK-Mel-28 (HTB-72) and FM45 (ECACC 13012410)/all skin melanomas. RC177 (kidney, renal cell carcinoma), MM909.11, MM909.15 and MM909.24 (all skin melanomas) were obtained from cancer patients treated at the Center for Cancer Immune Therapy (CCIT, Herlev Hospital, Copenhagen, Denmark).

(e) T Cell Clones

HLA-A*0201 restricted clone MELS/13 recognizing peptides EAAGIGILTV and ELAGIGILTV (heteroclitic L at position 2) from Melan A (Woodridge et al (2010); Lissina et al (2009)) and a canonical MAIT clone were cultured as described previously (Tungatt et al (2014)).

Gene Trapping by Whole Genome CRISPR

Figure 5:
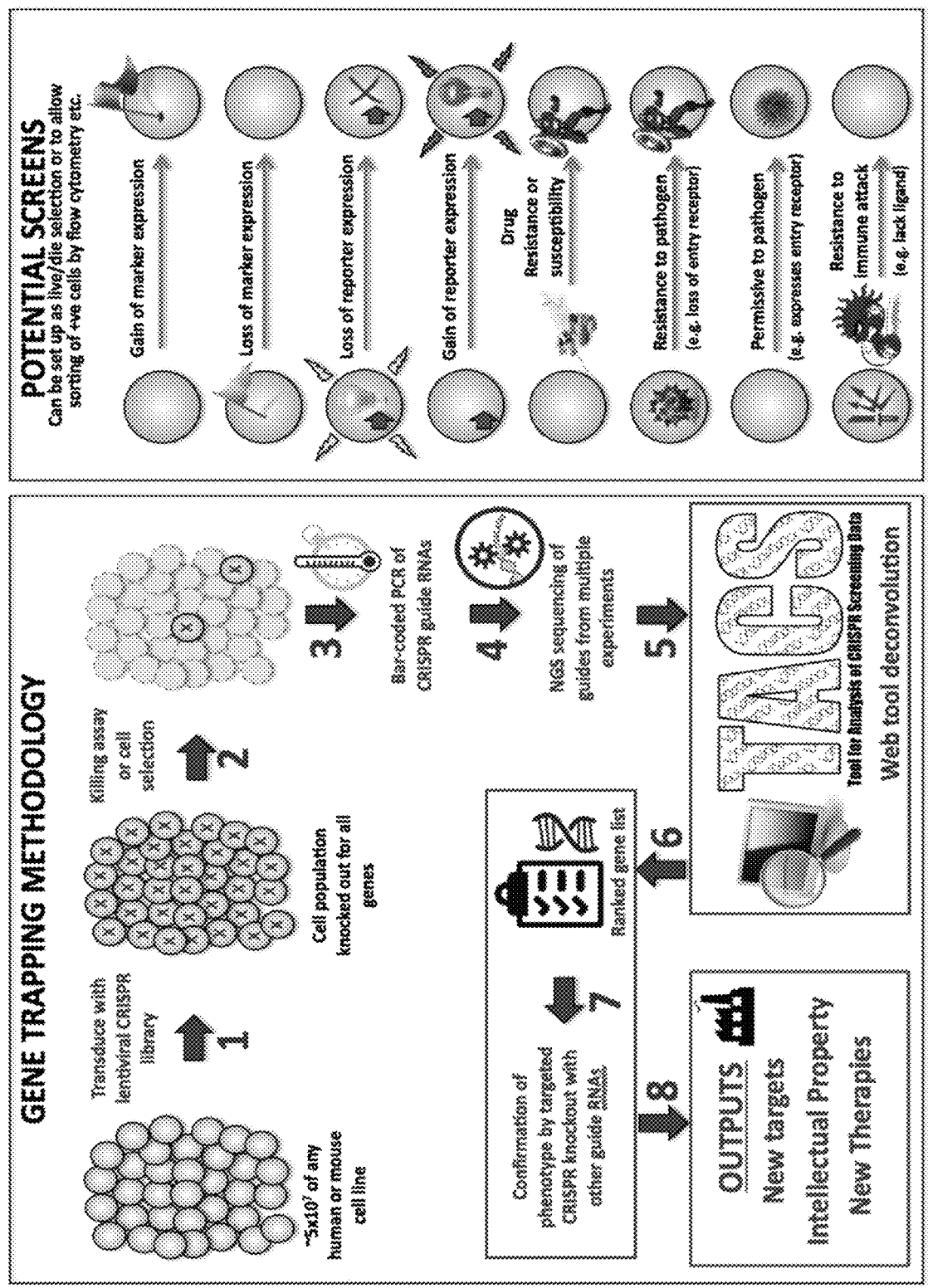

A whole genome CRISPR/Cas9 library approach was used (FIGS. 5 and 14 for an overview and also described recently (Patel et al., 2017)). Whole genome targeted HEK293 Ts using the GeCKO v2 sub-libraries A and B (Adgene plasmid, #1000000048, deposited by Dr. Feng Zhang) were used for selection by MC.7G.5. Briefly, successfully transduced HEK293 Ts (MOI of 0.4) selected with puromycin were co-incubated with MC.7G.5 at a predefined ratio of 1:1 for 2-3 weeks in 96 well flat-bottomed plates. Genomic DNA from HEK293 Ts that had survived two rounds of selection with MC.7G.5 was used for next generation sequencing to reveal inserted guide RNAs and therefore the genes that had been targeted for ablation.

Clone MC.7.G5 Shows Target Specificity Via MR1.

Figure 6:
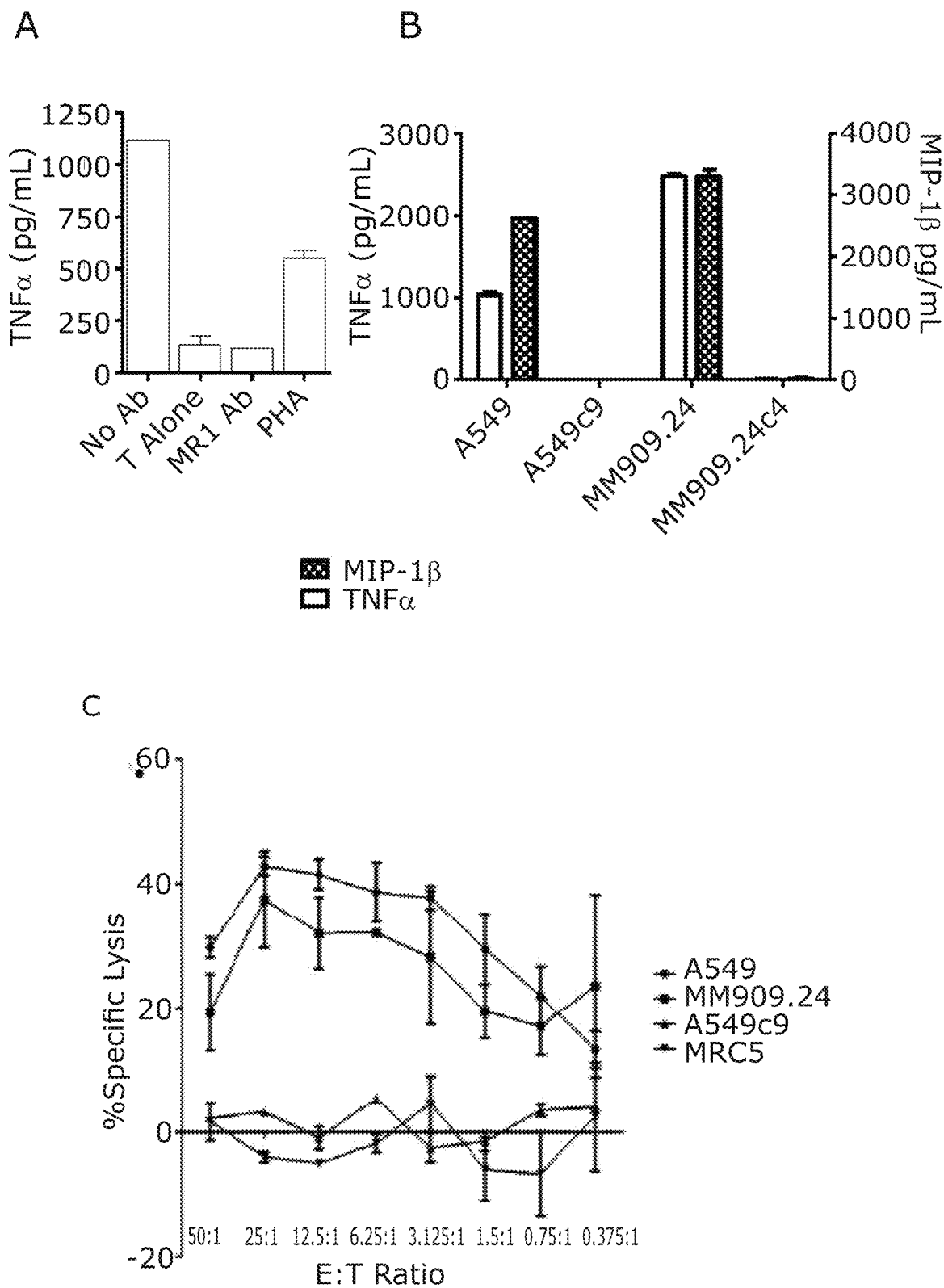
Figure 6:
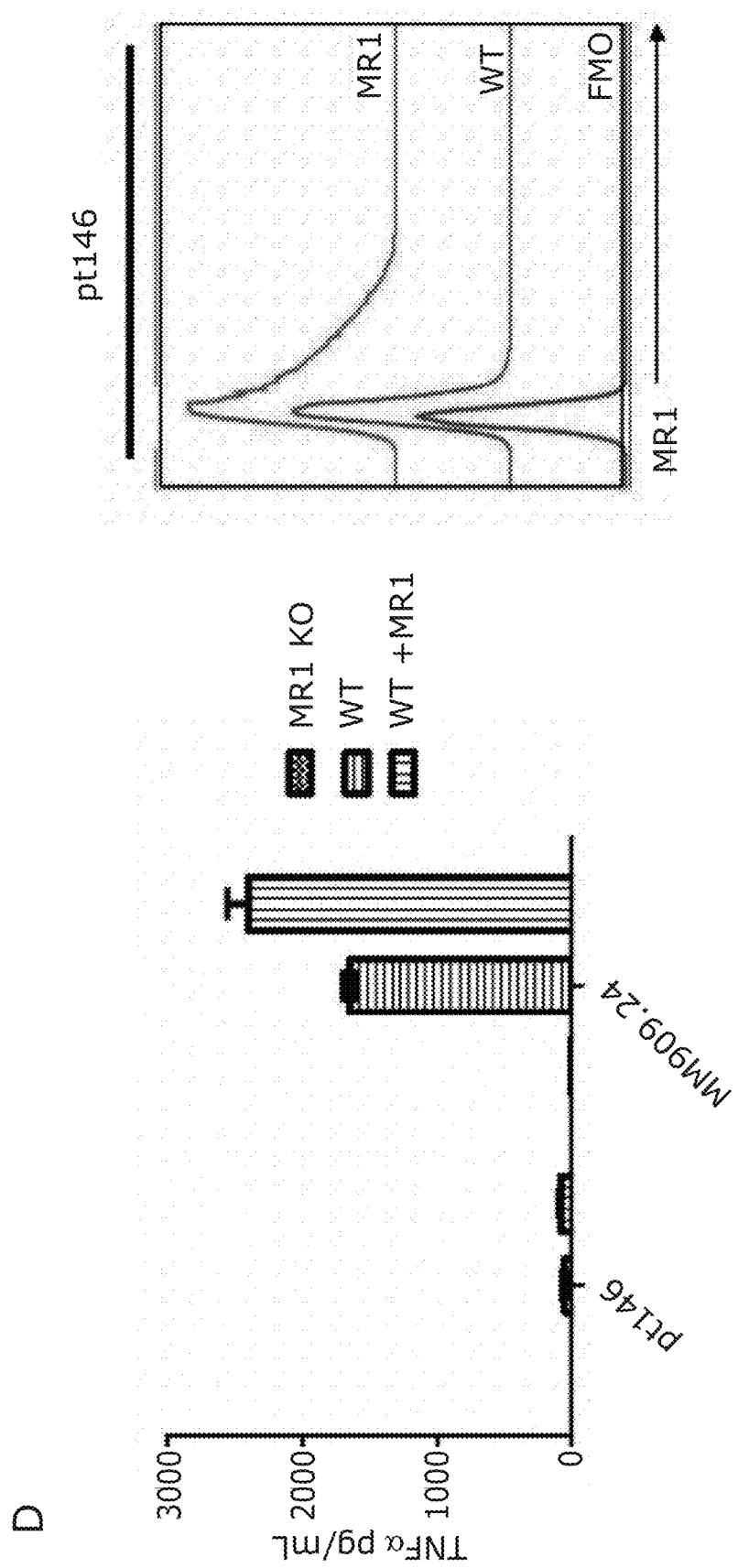

Using the same approach as above for MHC blocking Abs an activation assay was also performed using an anti-MR1 antibody, FIG. 6 and FIG. 14 (clone 26.5, BioLegend). MC.7.G5 was used in activation assay with A549 and MM909.24 cells that had been targeted with CRISPR/Cas9 technology to ablate expression of the MR1 gene as previously described (Laugel et al, 2016). Cell lines were used in activation and chromium release assays as above. A full-length codon optimised MR1 gene was generated as lentiviral particles and transduced in to target cells using similar methods (a single gene and no ratCD2 in this case) described below for the MC.7G.5 TCR, to create MR1 overexpressing (high) cell lines. MR1 expression was assessed using 10 µg/mL of the MR1 Ab (as above) and 50,000 cells per stain in 50 µL of PBS with 2% FBS. MR1 knockout in MM909.24 achieved as above described for A549s (6). Activation assays were performed as above with the cell lines: MM909.24 wt, MM909.24 MR1$^{-/-}$, MM909.24 MR1$^{High}$, pt146 wt (B-lymphoblastoid cell line), pt146 MR1$^{-/-}$ and pt146 MR1$^{High}$.

(g) Clone MC.7.G5 does not Stain with Tetrameric Forms of the MAIT Ligand MR1-5-OP-RU or with MR1-Ac-6-FP.

MC.7.G5 was harvest from culture, washed in PBS+2% FBS then treated with 50 nM of the protein kinase inhibitor (PKI), Dasatinib (Lissina et al., 2009), then labelled with PE conjugated tetramers assembled with MR1 refolded with either Ac-6-FP or 5-OP-RU, FIGS. 6 and 14. The tetramer stained cells were labelled with unconjugated anti-PE Ab as previously described (Tungatt et al., 2015), followed by Vivid and anti-CD8 Ab. A MR1-5-OP-RU reactive MAIT clone was stained in the same manner to act as positive control. Cells were gated on size then Vivid$^-$CD8$^+$ and displayed as histograms of tetramer fluorescence with data acquisition and analysis as above.

(h) Ac-6-FP and M. smeg Infection Reduces Recognition by Clone MC.7.G5 Despite Enhancing Expression of MR1 at the Cell Surface.

MC.7.G5 was used in an activation assay using targets cells (MM909.24 and A549) that had been pre-incubated with 50 µg/mL (FIG. 8), and 1, 10 or 100 µg/mL (FIG. 14), of Ac-6FP. Additionally, A549 cells that had been loaded with M. smeg were also used. Target cells that had been left untreated/not loaded were used as negative controls, FIGS. 8 and 14. A549s were incubated with M. smeg at an MOI of 100:1 M. smeg to A549s, for 2 h in antibiotic free medium followed by rinsing the cells in the culture flask and then culturing for 2 h in R10. MC.7.G5 and a MAIT clone were incubated for 4-5 h in the presence of the TNF processing inhibitor (TAPI)-0 (30 µM) and anti-CD107a Ab (H4A3, BD) then stained with anti-TNF Ab (cA2, Miltenyi Biotec), anti-CD3 Ab, anti-CD8 Ab and Vivid. Gating on size, single, vivid$^-$CD3$^+$ cells then CD8+ versus CD107a or TNFα with data acquisition and analysis as above. Each of the target cells was also stained with MR1 Ab post incubation with Ac-6FP or M. smeg at 10 µg/mL using 50,000 cells per stain in 50 µL of PBS with 2% FBS.

Transduction of polyclonal T-cells with the MC.7.G5 TCR (shown in FIG. 2) confers tumour recognition.

Codon optimized, full length TCR chains, separated by a self-cleaving 2A sequence, were synthesized (Genewiz) and cloned into the 3$^{rd}$ generation lentiviral transfer vector pELNS (kindly provided by Dr. James Riley, University of Pennsylvania, Pa.). The pELNS vector contains a rat CD2 (rCD2) marker gene separated from the TCR by another self-cleaving 2A sequence. Lentiviral particles were generated by calcium chloride transfection of HEK293T cells. TCR transfer vectors were co-transfected with packaging and envelope plasmids pMD2.G, pRSV-Rev and pMDLg/pRRE. Lentiviral particles were concentrated by ultracentrifugation prior to transduction of CD8+ T-cells using 5 µg/ml of polybrene, with the CD8+ T-cells purified by magnetic separation (Miltenyi Biotec) from healthy donors (FIG. 9) or melanoma patients (FIG. 15) 24 h in advance and activated overnight with CD3/CD28 beads (Dynabeads, Life Technologies) at 3:1 bead:T-cell ratio. T-cells that had taken up the virus were selected by enrichment with anti-rCD2 PE Ab (OX-34, BioLegend) followed by anti-PE magnetic beads (Miltenyi Biotec). 14 d post transduction T-cells were expanded with allogeneic feeders. For all functional experiments, MC.7.G5 TCR transduced T-cells were >95% rCD2+ and used for functional analysis (FIG. 16). Transduced cells were incubated with target cells for 4-5 h in the presence of 30 mM of TAPI-0 CD107a Ab and then stained with Abs for TNFα, CD3, CD8 and also Vivid. Gating on size, single, vivid$^-$CD3$^+$ cells and then CD8+ versus CD107a or TNF α. Data acquisition and analysis as above. The TCR transduced T-cells from patients were also used for chromium release cytotoxicity assays (FIG. 15), as described above.

Flow Cytometry

Cells were stained with Fixable Live/Dead Violet Dye (Life Technologies) and the following surface antibodies:

pan-αβ TCR PE (clone IP26, Biolegend), pan-γδ TCR-FITC (clone REA591, Miltenyi Biotec), CD3 PerCP (clone UCHT1, Biolegend), CD4 APC (clone VIT4, Miltenyi Biotec), CD8 PE (clone BW135/80, Miltenyi Biotec), rat CD2 PE (clone OX-34, Biolegend) and MR1 PE (clone 26.5, Biolegend). For staining with MR1 PE, Fc Block (Miltenyi Biotec) was used according to manufacturer's instructions. For tetramer staining, MR1 monomers were provided by Jamie Rossjohn (Monash University), and pMHC monomers produced in-house. Tetramers were assembled and used for optimized staining as described previously (Tungatt et al (2014)). Data was acquired on a BD FACS Canto II (BD Biosciences) and analysed with FlowJo software (TreeStar).

MR1 Knockout and Transgene Expression

MR1 sgRNA and CRISPR/Cas9 lentivirus was produced and used as described previously (Laugel et al (2016)). The MR1 transgene was cloned into the second generation pRRL.sin.cppt.pgk-gfp.wpre lentivector backbone developed by Didier Trono's laboratory (Addgene no. 12252) devoid of the human PGK promoter and GFP cDNA, and lentiviral particles produced as described for MR1 sgRNA (Laugel et al (2016)). Target cells were spinfected in the presence of 8 μg/mL polybrene; 500×g for 2 hours at 37° C. (Shalem et al (2014)). Anti-MR1 antibody PE (clone 26.2, Biolegend) positive cells were magnetically enriched using anti-PE magnetic beads according to manufacturer's instructions (Miltenyi Biotec).

TCR Sequencing and Transduction

MC.7.G5 TCR was sequenced in-house using the SMARTer RACE kit (Clontech) and 2-step polymerase chain reaction using universal forward primers and reverse primers specific for TCR-α and TCR-β constant regions. The TCR was then synthesised with codon optimisation (Genewiz), with full length TCR chains separated by a self-cleaving 2A sequence (Ryan et al 1991). The TCR was cloned into the third generation pELNS lentiviral vector (kindly provided by James Riley, University of Pennsylvania) which contains rCD2 separated from the TCR by a second 2A self-cleavage sequence. Lentiviral particles were generated by calcium chloride transfection of HEK293T cells and concentrated by ultra-centrifugation. Post therapy PBMCs were obtained from TIL patients MM909.11 and MM909.24 and CD8 and CD4 T cells purified by magnetic enrichment (Miltenyi Biotec). T cells were subsequently activated by overnight incubation with CD3/CD28 beads (Dynabeads; Life Technologies) at a 3:1 bead-to-T-cell ratio. T-cells were then transduced with MC.7.G5 TCR in the presence of 5 μg/mL polybrene (Santa Cruz Biotechnology). T cells that had taken up the virus were magnetically enrichment with anti-rCD2 antibody and anti-PE magnetic beads, according to manufacturer's instructions (Miltenyi Biotec). 14 days post transduction, T cells were expanded as described previously (Tungatt et al (2014)). For all functional experiments, transduced T cells were >85% rCD2+ (FIG. 16D).

Whole Genome GeCKOv.2 Screening

Lentiviral particles for the GeCKOv.2 library (plasmid kindly provided by Feng Zhang (Sanjana et al (2014)) (Addgene plasmid #1000000048)). The GeCKOv.2 library consists of 123,411 single guide (sg)RNAs targeting 19,050 protein-coding genes (6 sgRNAs per gene) and 1,864 microRNAs (4 sgRNAs per microRNA) and was used as lentivirus to transduce the target cell line HEK293T. 4×10$^7$ HEK-293T cells were transduced with an MOI of 0.4 to provide 100× coverage of each sublibrary. Cells that had taken up the lentivirus were selected under puromycin. After 14 days, half the library was frozen as a control. MC.7.G5 was added to remaining transduced HEK-293T cells at a T-cell to HEK293T ratio of 0.25:1 in 20 IU IL-2 media. After 14 days, MC.7.G5 was added again at a 0.5:1 ratio. After 7 days the HEK293T cells were used for sequencing. Genomic DNA from 3×10$^7$ of HEK-293T cells (unselected control and selected with MC.7.G5) was isolated (GenElute Mammalian Genomic DNA Miniprep Kit, Sigma Aldrich). The entirety of isolated genomic DNA (2.5 μg per 50 μl reaction) was used for subsequent PCR, to ensure capturing the full representation of the libraries. The two step PCR was performed as described before (Shalem et al (2014)), using HPLC purified primers and NEBNext High Fidelity PCR MasterMix (New England BioLabs). The <300 bp PCR products were subsequently isolated from the agarose gel and sequenced on HiSeq instrument (Illumina), with 80 cycles of read 1 (to determine the sequence of sgRNAs) and 8 cycles of read 2 (to identify sample-specific barcode). Analysis of enriched guides was performed using MAGeCK analysis (Li et al (2014)).

Long-Term Killing Assay

For flow-based killing assays 5000-10,000 of a cancer or normal cell line was placed in 96 U well plates, and MC.7.G5 clone added to give five T-cells per target cell (experimental wells). The cells were co-cultured in 200 μL of target cell media supplemented with 20 IU of IL-2 and 25 ng/mL of IL-15. Targets cells (control wells), MC.7.G5 and CSFE C[I]1 Rs were also cultured alone to aid analysis. The cells were incubated for 48 hours. For sensitivity assays the number of MC.7.G5 was titrated relative to the target cells and incubated for 7 days. In addition to cell lines described elsewhere in the materials and methods section, the ovarian cancer cell line A2780 (ECACC 93112519) was also used. Prior to harvest, 0.1×10$^6$ CFSE labelled (0.1 μM) C[I]1R cells were added to each well to allow the number of target cells that remained in experimental and control wells to be established. The cells were washed three times with chilled D-PBS supplemented with 2 mM EDTA then stained in the assay plates with Fixable Live/Dead Violet Dye (Life Technologies) then CD3 PerCP (clone UCHT1, BioLegend) and/or anti-TRBV25.1 APC TCR (TRBV11 Arden nomenclature: catalogue A66905, Beckman Coulter) Abs to allow dead cells and T-cells to be gated-out leaving viable target cells for analyses. The percentage killing was calculated using the following equation:

$$\% \text{ killing} = 100 - ((\text{experimental target cell events} \div \text{experimental bead or } CFSECIR \text{ events}) \div (\text{control target cell events} \div \text{control bead or } CFSECIR \text{ events}) \times 100)$$

Activation Assays with C[I]1Rs Cells Expression Empty (K43A) MR1

C[I]1R cells were transduced with MR1 carrying the K43A mutation (R. Reantragoon et al) as for wild-type MR1. Activation assays and flow cytometry were performed as described elsewhere in the material and methods section.

Results

Clone Characterisation

Figure 1:
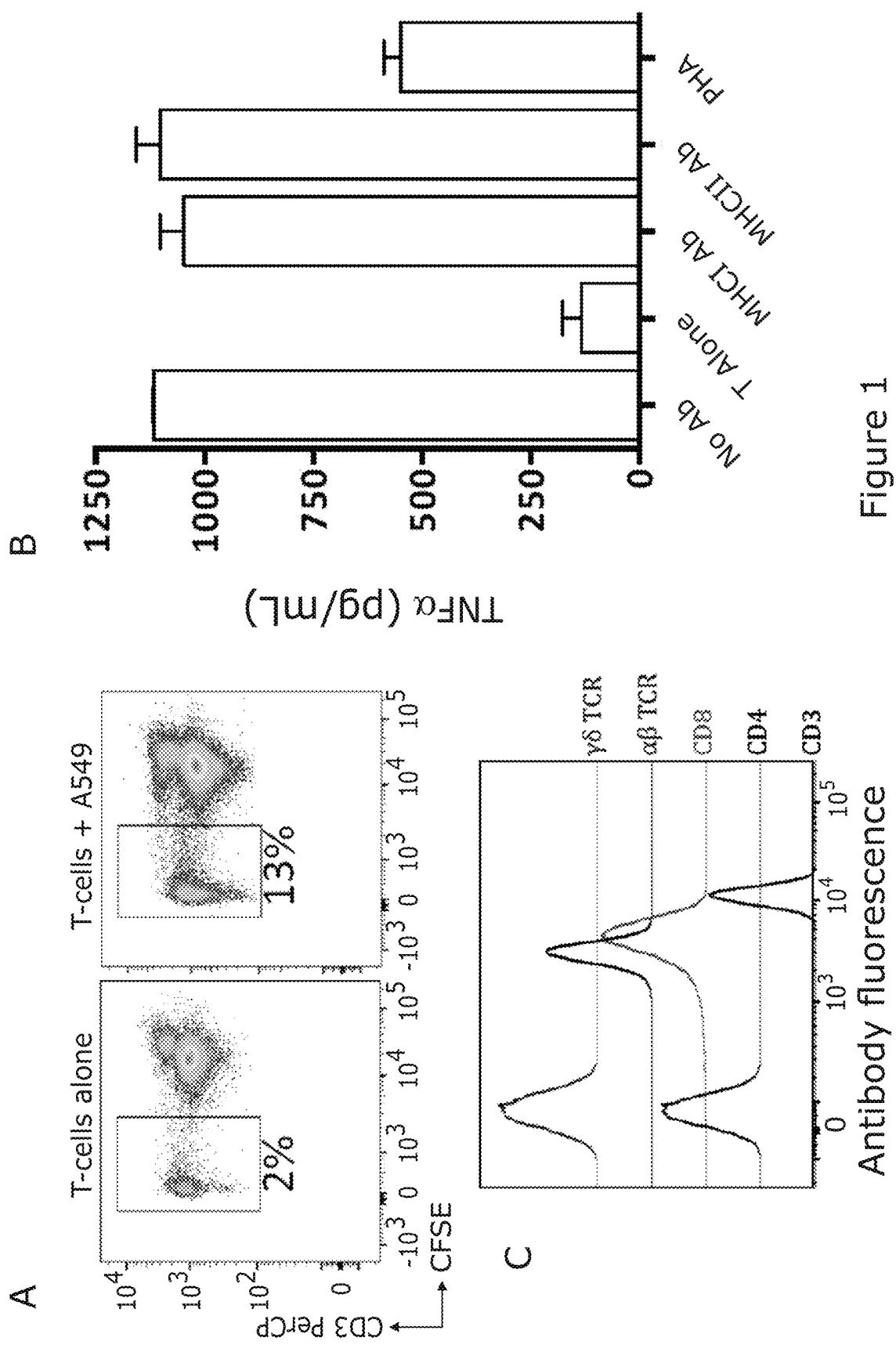

1. T-cell clone MC.7.G5 recognises A549 cells (FIG. 1A). Addition of 10 μg/ml of blocking MHC-I and MHC-II antibodies did not block recognition (FIG. 1B).

2. Antibody staining and flow cytometry confirmed that clone MC.7.G5 expresses an αβ TCR and is CD8+ (FIG. 1C and repeated in FIG. 16A).

Figure 2:
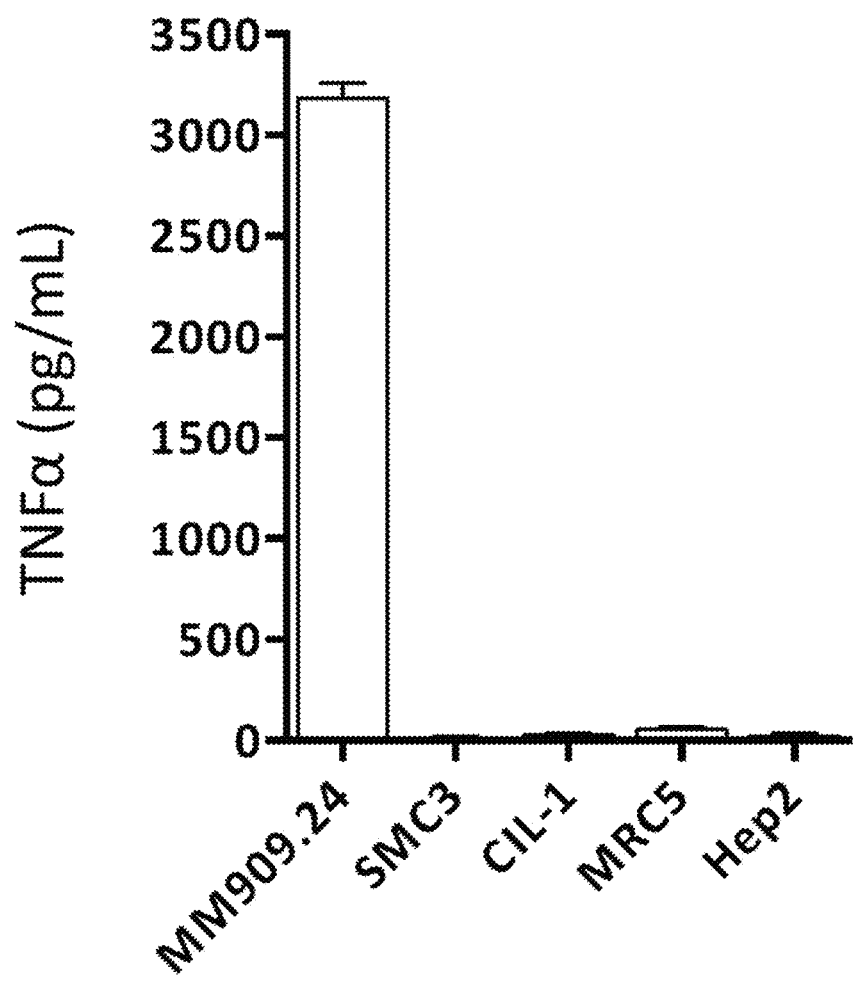

3. Importantly T-cell clone MC.7G.5 does not respond to normal (non-cancer) cell lines (FIG. 2 and FIGS. 17B&C). When the MC.7.G5 TCR was expressed in primary CD8 T-cells it did not mediate killing of normal cells (FIG. 15B). The MC.7.G5 clone did not respond to itself or fresh peripheral blood mononuclear cells (not shown). The MC.7G.5 T-cell clone was isolated from a normal healthy donor where it was doing no obvious damage. We conclude that T-cell clone MC.7G.5 is tumour-specific.

4. The MC.7.G5 T-cell clone expresses a TCR made from TRAV38.2/DV8 TRAJ31 and TRBV25.1 TRBJ2.3 of sequence shown in FIG. 3. MR1-restricted clone MC.7.G5 is not a MAIT and it does not express the MAIT TCRα chain.

5. The MC.7.G5 T-cell clone makes MIP1β (FIG. 4A) and TNFα (FIG. 4A) in response to a wide range of cancer cell lines. MC.7.G5 is also highly cytotoxic towards many cancer cells (FIGS. 4B and 17A) even at very low effector to target ratios (FIGS. 4B and 17C). MC.7G.5 recognised all types of cancers tested: blood, bone, melanoma (skin), colon, kidney, lung, cervical, breast, ovarian and prostate. Moreover, this cytotoxicity was effective and sensitive: data from a long-term (48 hours) killing assay showed >95% killing of cancer cell lines (FIG. 17A) and at low T-cell to target cell ratios (FIG. 17C).

6. Whole genome CRISPR/Cas9 libraries of a MC.7.G5 cancer target revealed MR1 as the ligand of MC.7.G5 by creating a target line that was resistant to lysis by clone MC.7.G5. Sequencing of the guide RNAs in this resistant line showed that they mainly targeted genes involved in metabolism and the immune system. Guide RNAs for MR1 and β2 microglobulin were highly enriched in the cell population that were resistant to lysis by MC.7.G5. These genes immediately caught our attention due to their linkage to MAIT cell activation (MR1 requires β2 microglobulin in order to fold).

7. Blocking with an anti-MR1 antibody ablated recognition of the A549 cell line (FIG. 6A and repeated in FIG. 14).

6. Cancer cell lines A549 (clone c9) and MM909.24 (clone c4), were not recognised when MR1 is knocked out from these lines (FIGS. 6B&C and 14). Over expression of MR1 in MM909.24 via lentiviral transduction slightly enhances recognition (FIGS. 6D and 14).

8. LCL line pt146 is not recognised by T-cell clone MC.7.G5. MC.7.G5 also fails to recognise pt146 cells even when they are transduced with an MR1-expressing lentivirus and exhibit some MR1 expression at the cell surface. LCL line pt146 does not express the MC.7.G5 T-cell ligand. This suggest that MC.7.G5 is not responding to MR1 per se but rather that it is recognising a unique cancer specific ligand within the MR1 binding groove (FIG. 6).

Figure 7:
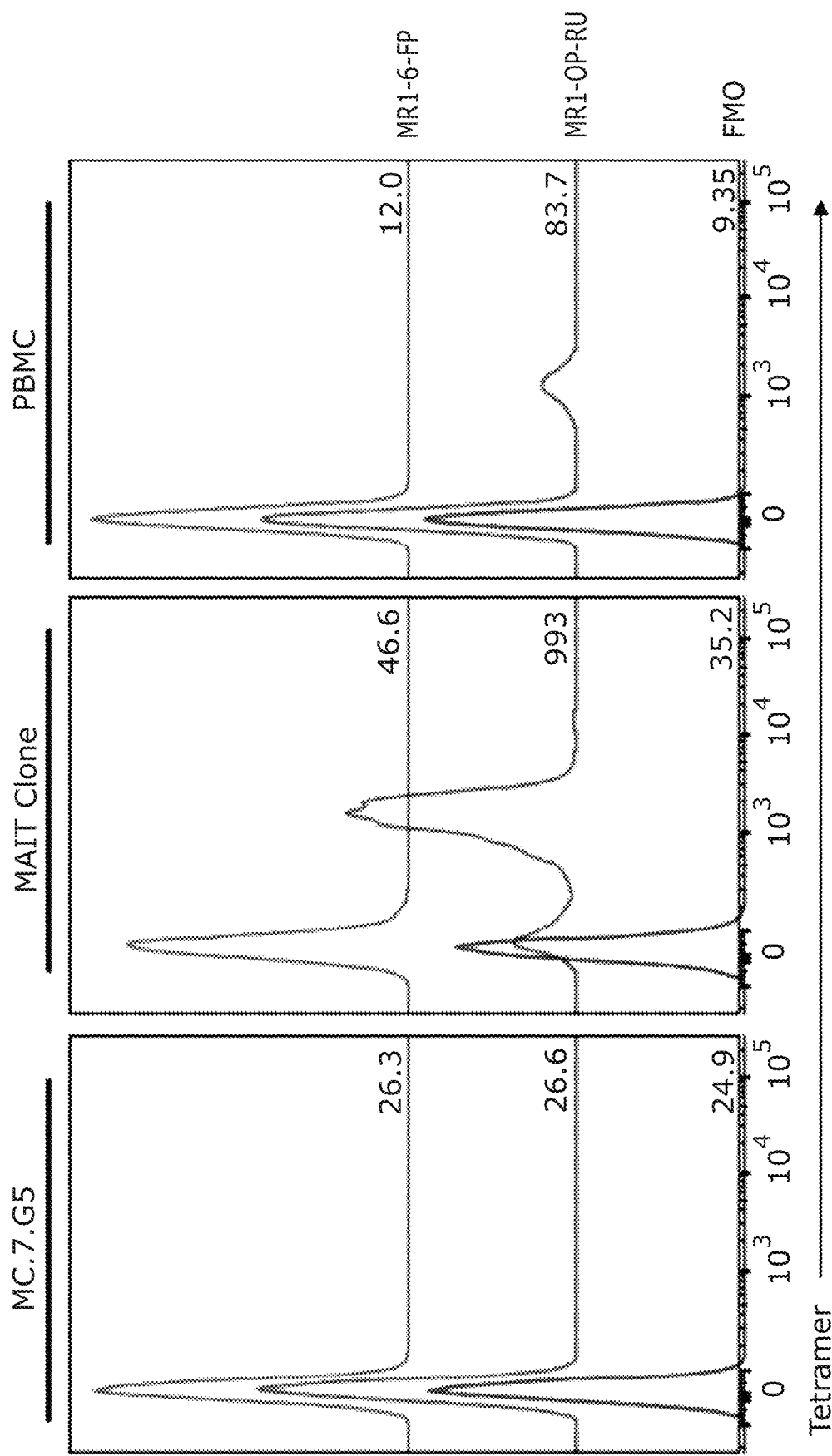

9. Clone MC.7.G5 does not stain with Ac-6-FP or 5-OP-RU loaded MR1 tetramers (FIG. 7 and repeated in FIG. 14E). MAIT T-cell clones stain with MR1-5-OP-RU tetramers in a parallel assay. We conclude that MC.7.G5 does not bind to MAIT ligands. This finding is consistent with MC.7.G5 not expressing the canonical MAIT invariant TRAV1-2 α chain. This was corroborated using 'empty' (K43A) MR1 tetramers, which did not stain MC.7.G5. The K43A mutation of MR1 allows refolding of MR1 in the absence of a bound cargo, FIG. 14. Similarly, expression of empty (K43A) MR1 does not lead to recognition by MC.7.G5 despite good cell surface expression of MR1 on the C1Rs (MR1 Ab staining right panel) FIG. 18. This further demonstrates that a cancer-expressed ligand bound to MR1 is important for MC.7.G5 activation.

Figure 8:
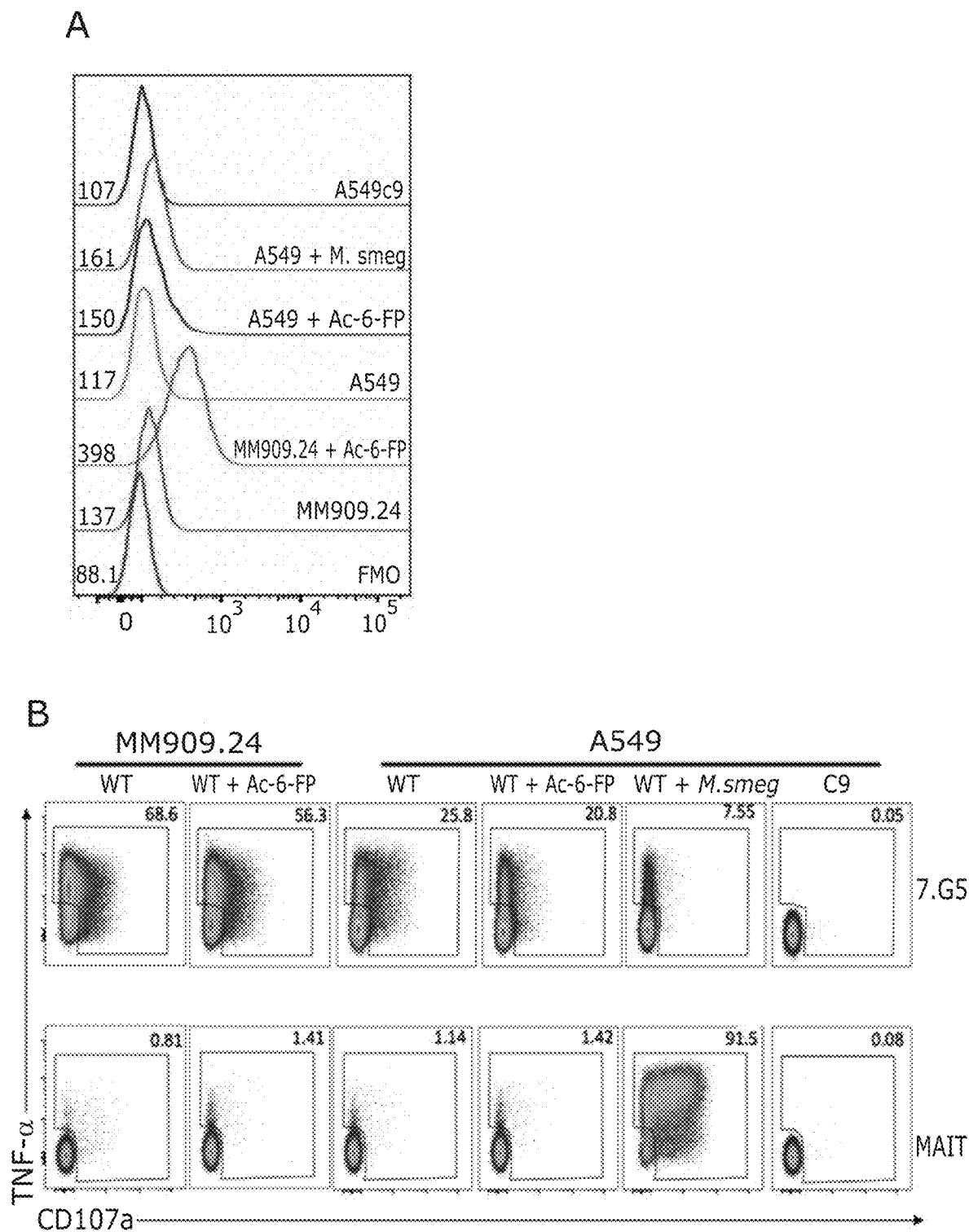

10. Addition of 10, 50 or 100 μg/mL of MR1 ligand Ac-6-FP (http://www.rcsb.org/pdb/explore.do?structureId=4pj5) for 12 hours substantially enhances MR1 expression at the surface of MM909.24 cells (FIGS. 8 and 14G) but lowers the recognition of these cells by clone MC.7.G5 (FIGS. 8 and 14G). This finding strongly suggests that clone MC.7.G5 is recognizing an MR1-bound ligand that is different from Ac-6-FP on the MM909.24 cell surface. Similar findings were observed with A549 cells. Incubation of A549 cells with Ac-6-FP reduced recognition while increasing MR1 expression on the surface. Exposure of A549 cells to *Mycobacterium smegmatis* (*M. smeg*) also enhanced MR1 expression. This is expected as it is known that *M. smeg* produces MR1 ligands. These ligands can be recognized by MAIT cells. *M. smeg* infected A549 cells were a good ligand for a MAIT clone in a parallel experiment (FIGS. 8 and 14F). Exposure of A549 cells to *M. smeg* substantially reduced recognition by clone MC.7.G5. We conclude that clone MC.7.G5 recognizes cancer cells via a ligand in the MR1 binding groove that is only present on cancer cells.

Figure 9:
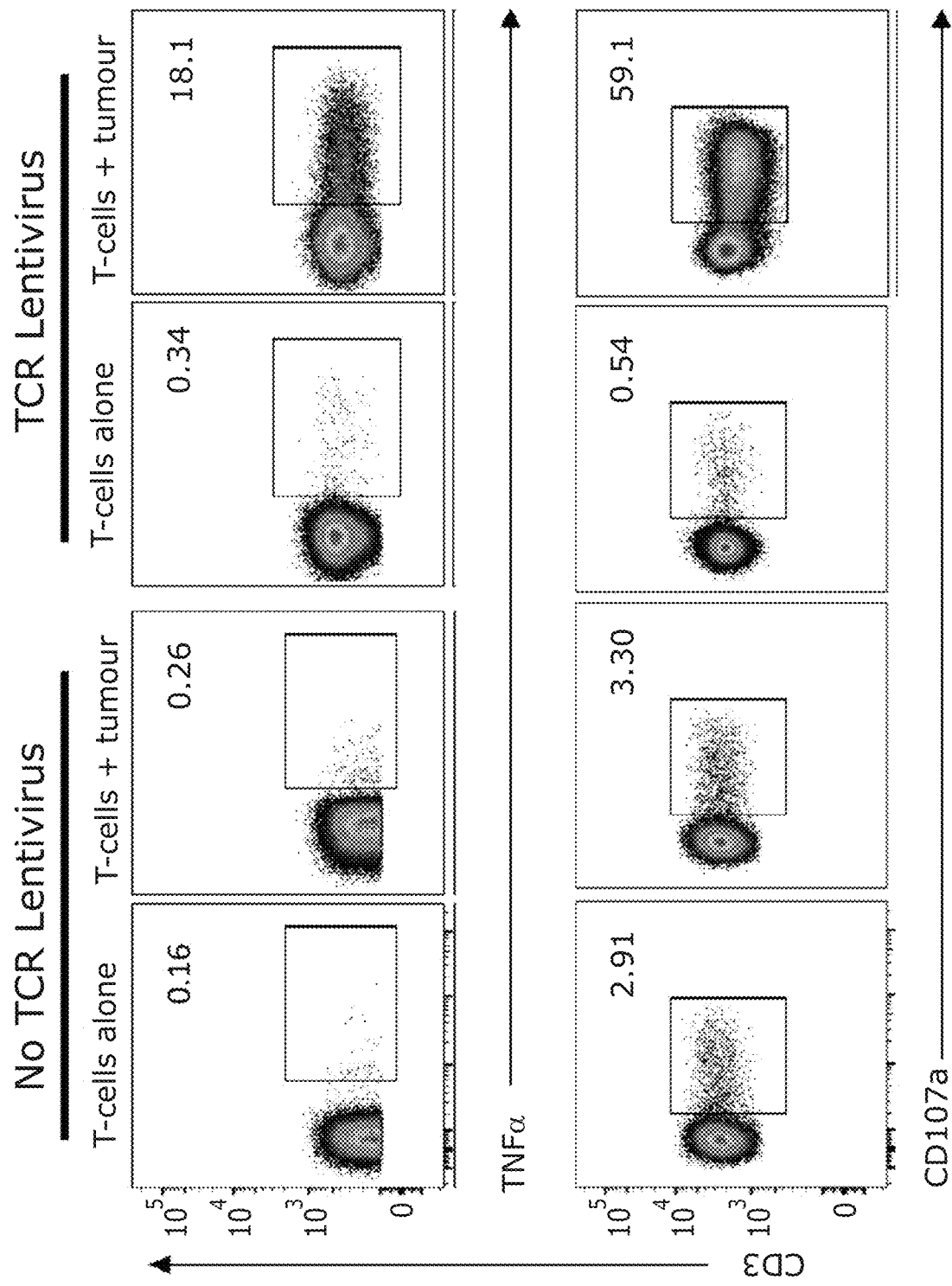
FIG. 9 shows transduction of polyclonal T-cells with the MC.7.G5 TCR (shown in FIG. 2) confers tumour recognition. Further experiments with the MC.7.G5 TCR and patient T-cells are shown in FIG. 15.

11. Transduction of the MC.7.G5 into polyclonal T-cells allows them to recognise tumour targets (FIG. 9). Indeed, CD8 T-cells from metastatic melanoma patient MM909.11 transduced with the MC.7.G5 TCR killed autologous and non-autologous melanomas, but not normal cells (FIG. 15). We conclude that tumour recognition by clone MC.7.G5 occurs via the MC.7.G5 T-cell receptor shown in FIG. 3 via a ligand presented by the MR1 molecule.

A genome-wide CRISPR/Cas9 approach, using the GeCKOv.2 library which targets every protein-coding gene in the human genome with six different single guide (sg) RNAs, was used to identify genes essential for recognition of target cells by MC.7.G5 (FIG. 13A). Following two rounds of selection with MC.7.G5 the surviving transduced HEK293T cells exhibited reduced capacity to stimulate MC.7.G5, suggesting key genes involved in their recognition had been ablated (FIG. 13B). Sequencing of the CRISPR sgRNAs in the lysis resistant HEK293T cells showed that only 6 genes were targeted by more than one enriched sgRNA: β2M (five sgRNAs), MR1 (two sgRNAs), regulatory factor X (RFX, five sgRNAs), RFX associated ankyrin containing protein (RFXANK, five sgRNAs), RFX associated protein (RFXAP, three sgRNAs), and signal transducer and activator of transcription 6 (STATE, two sgRNAs) (FIG. 13C). RFX, RFXANK and RFXAP are essential components of the protein complex responsible for transactivating β2M, MHCI and MHCII promoters. Combined with the fact that β2M and MR1 unite to form a non-polymorphic stable antigen-presenting molecule known to activate MAITs and other MR1-restricted T-cells, these data strongly suggested that the MC.7.G5 T-cell recognized cancer targets via the invariant MR1 molecule. Accordingly, MR1 antibody, but not MHCI or MHCII antibodies, blocked target cell recognition by MC.7.G5 (FIG. 14A). CRISPR mediated knockout of MR1 from A549 and melanoma MM909.24 (deletion mutation shown in FIG. 16B) protected against MC.7.G5-mediated recognition and lysis (FIG. 14B). Melanoma MM909.24 did not stain with anti-MR1 antibody suggesting that very minimal levels of MR1 were required for target recognition (FIG. 16C). Overexpression of MR1 resulted in strong recognition of the poorly recognized targets, HeLa and C1R, and slightly enhanced recognition of melanoma MM909.24 (FIG. 14C). Reintroduction of MR1 in to CRISPR/Cas9 MR1-knockout A549 cells restored recognition by MC.7.G5 (FIG. 14D), instilling further confidence that cancer cell recognition was MR1-dependent.

MR1 is known to present intermediates in riboflavin synthesis at the cell surface to MAIT cells and is not believed to be expressed at the cell surface without a bound cargo. MC.7.G5 did not stain with tetramers composed of MR1 containing the K43A mutation that allows MR1 refolding without bound ligand. The MR1-dependent recognition of cancer cells suggested that MC.7.G5 might recognize an MR1-bound metabolite that was specifically expressed or upregulated in malignant cells. In concordance with this hypothesis, MC.7.G5 did not stain with tetramers assembled with MR1 presenting microbial derived T cell activator 5-OP-RU. Furthermore, recognition of target cells was reduced when loaded with either the MAIT activating bacterium *Mycobacterium smegmatis* (*M. smeg*) (FIG. 14F), or MR1 ligand Acetyl-6-Formylpterin (Ac-6-FP) (22, 23) (FIG. 14G), despite an increase in surface expression of MR1 (FIG. 14G). These results indicate that MC.7G.5 does not recognize MR1 per se, nor MR1 by known mechanisms, but rather MR1 with bound cargo that is specific to, or associated with, cancer cells.

TCR sequencing of MC.7.G5 revealed a novel TCR comprised of a TRAV38.2/DV8 TRAJ31 α-chain paired with a TRBV25.1 TRBJ2.3 β-chain. To explore the therapeutic potential of targeting MR1 on cancer cells we purified T-cells from the PBMCs of Stage IV melanoma patients and lentivirally transduced them with the MC.7.G5 TCR, which resulted in recognition and killing of autologous and non-autologous melanomas (FIG. 15), but not healthy cells (FIG. 15B). The killing was specific to MR1 as the MC.7.G5 TCR transduced cells did not lyse MR1 knockout melanomas (FIG. 15B). We conclude that the MC.7.G5 TCR can redirect patient T-cells to kill patient cancer cells without the requirement of a specific HLA. MR1 is an attractive target for cancer immunotherapy due to its non-polymorphic, ubiquitously expressed nature. Recent advances in MR1 tetramers and ligand discoveries have progressed knowledge in this area but there is still much to be discovered. Here we confirmed cancer cell recognition by a T-cell clone that responded to multiple cancer cell lines from diverse tissue types.

Long term killing assays (FIG. 17) show MC.7.G5 killing of a range of cancer cell lines of different origin. In fact, MC.7.G5 was capable of killing 95-99.9% of each cell line. Further, MC.7.G5 did not kill healthy cells.

Overexpression of mutated K43A ('empty') MR1 in C1Rs cells did not lead to activation of M.7.G5 (FIG. 18A) despite high staining of the C1Rs-K43A with MR1 antibody (FIG. 18B). In contrast, overexpression of wild-type MR1 in C1 Rs induced MC.7.G5 activation. This demonstrates that the MC.7.G5 TCR recognizes MR1 with a bound cargo.

Current MR1 antibodies are unable to detect low surface expression of MR1 on cancer cells, despite detectable mRNA expression. Indeed, the level of MR1 surface expression required for cancer cell recognition by MC.7.G5 was often below the threshold required for staining with antibody, suggesting that the MC.7.G5 TCR might be capable of responding to a low copy number of MR1 ligand, akin to T-cells that recognize pMHC. Our results also demonstrate the immense power of genome-wide CRISPR/Cas9 screening as a discovery platform for unconventional T-cell ligands. Indeed, we have also used this technique to find obligate cell surface expressed molecules required for cancer cell recognition by γδ TCRs and we anticipate the methodologies applied here will rapidly revolutionize the unconventional T-cell field by revealing new ligands.

In summary, whole genome CRISPR screening was used to reveal the cancer expressed ligand of MC.7.G5. MR1 validation experiments showed that activation of MC.7.G5 by A549 cells could be blocked by MR1 antibody and the clone did not respond to MR1 knockout A549 cell created by our laboratory (Laugel et al 2012) or a CRISPR/Cas9-mediate MR1 knockout of the melanoma target MM9909.24. MC.7.G5 responded to most cancer cell lines but did not respond to primary (non-tumour) cells. Recognition of target cancer cells by MC.7.G5 required the expression of MR1. The only polymorphism in MR1 is silent (Parra-Cuadrado et al 2000) such that MR1-restricted TCRs can respond to the cells from any individual in the population. This makes MR1 a particularly attractive candidate for adoptive cell therapy approaches as a single product could be used in all patients (Guo et al 2015).

CONCLUSION

Figure 10:
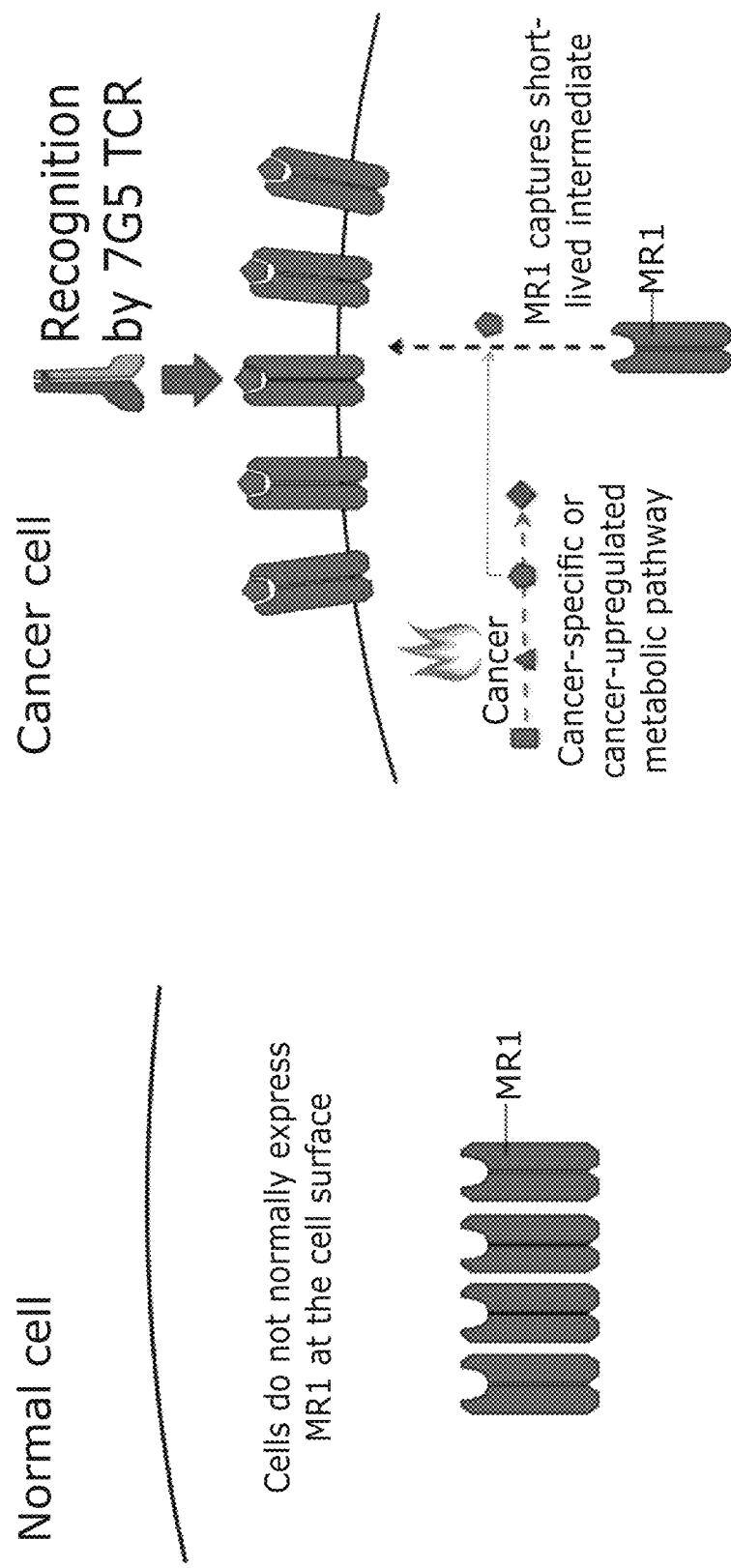
FIG. 10 is a schematic showing the clone MC.7.G5 TCR only recognises cancer cells. Recognition requires MR1 and is inhibited by known non-cancer MR1 ligands suggesting that MR1 presents a cancer-specific, or cancer-upregulated, ligand to the MC.7.G5 TCR.
Figure 11:
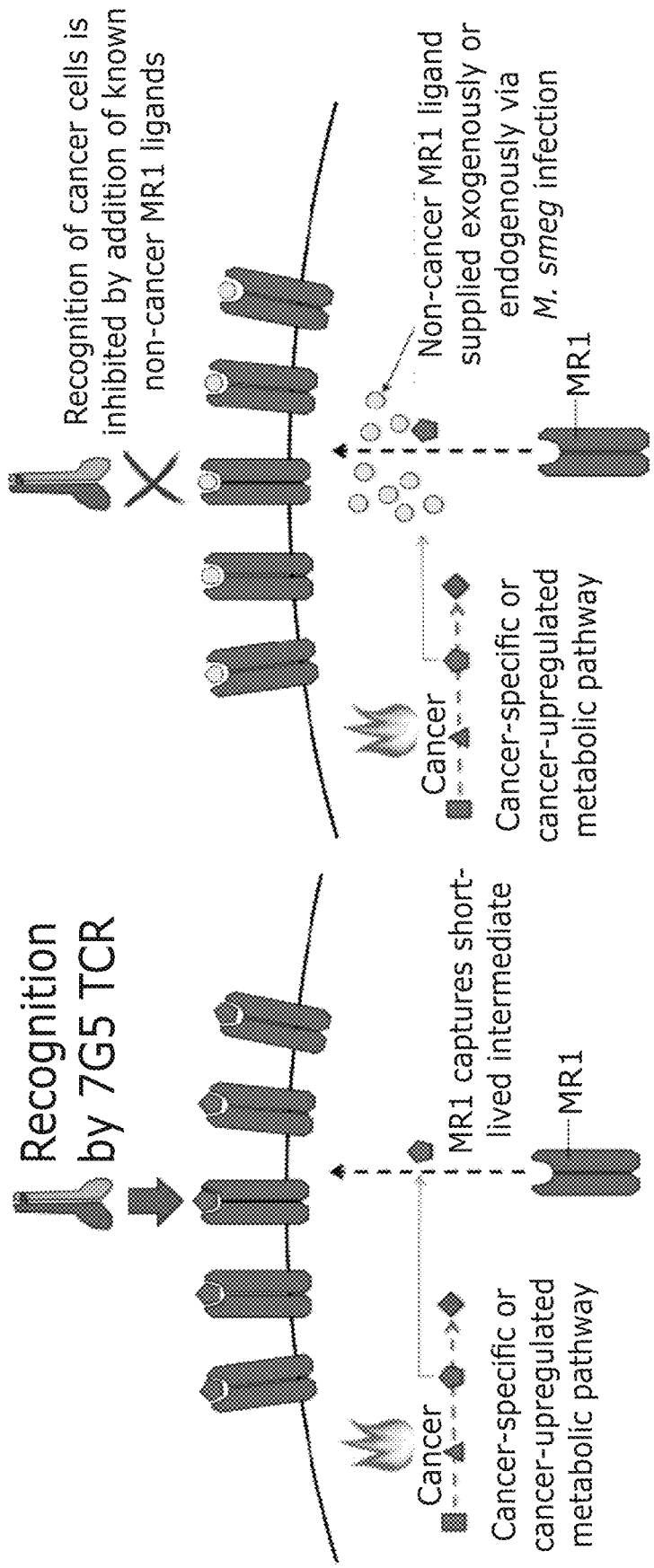
FIG. 11 is a schematic showing Known MR1 ligands inhibit recognition of cancer cells by MC.7.G5 TCR.

The MC.7.G5 TCR enables T-cells to recognise a wide range of tumours. Recognition occurs via population invariant molecule MR1. MR1 is not normally expressed on the cell surface in the absence of a ligand in its binding groove (Chua et al. 2011). Expression of a ligand that binds to MR1 allows the molecule to traffic to the cell surface to present this ligand (FIG. 10). Addition of known MR1 ligands reduces tumour recognition by the MC.7.G5 T-cell clone and suggests that the MC.7.G5 recognises a cancer-cell specific ligand in the context of MR1 (FIG. 11) (i.e. other ligands compete with the cancer ligand for binding to MR1). Given what is known about MR1, it seems likely that this ligand is an intermediate in a metabolic pathway that is upregulated by tumorigenesis. Ongoing experiments are aimed at determining the nature of this ligand.

This invention centres around the TCR identified in T-cell clone MC.7.G5. This TCR recognises a wide range of cancer cells through the conserved MHC related (MR) 1 protein. This TCR does not recognise non-tumour cells. CRISPR/Cas9 knockout of MR1 from tumour lines or blocking with anti-MR1 antibody removes TCR recognition. Incubation with known MR1-binding ligands reduces TCR recognition suggesting that the T-cell receptor (TCR) ligand is a cancer-specific metabolite that sits or is presented to the TCR in the MR1 binding groove. The MC.7.G5 TCR can be used in a variety of different cancer immunotherapy strategies. The broad tumour recognition and human leukocyte antigen (HLA)-independence of recognition unlocks exciting possibilities for pan-cancer, pan-population immunotherapies using this TCR.

REFERENCES

Chua W J, Kim S, Myers N, Huang S, Yu L, Fremont D H, et al. (2011) Endogenous MHC-related protein 1 is transiently expressed on the plasma membrane in a conformation that activates mucosal-associated invariant T cells. Journal of Immunology, 186, 4744-50.

Ekeruche-Makinde, J., M. Clement, D. K. Cole, E. S. J. Edwards, K. Ladell, J. J. Miles, K. K. Matthews, A. Fuller, K. A. Lloyd, F. Madura, G. M. Dolton, J. Pentier, A. Lissina, E. Gostick, T. K. Baxter, B. M. Baker, P. J. Rizkallah, D. A Price, L. Wooldridge and A. K. Sewell (2012). T cell receptor optimized skewing of the repertoire can enhance antigen targeting. Journal of Biological Chemistry, 287, 37269-81.

Guo T, Chamoto K, Hirano N. (2015) Adoptive T Cell Therapy Targeting CD1 and MR1. Frontiers in immunology. 6:247.

Laugel B, Lloyd A, Meermeier E W, Crowther M D, Connor T R, Dolton G, et al. (2016) Engineering of Isogenic Cells Deficient for MR1 with a CRISPR/Cas9 Lentiviral System: Tools To Study Microbial Antigen Processing and Presentation to Human MR1-Restricted T Cells. Journal of Immunology, 197, 971-82.

Li W., H. Xu, T. Xiao, L. Cong, M. I. Love, F. Zhang, R. A. Irizarry, J. S. Liu, M. Brown, X. S. Liu, (2014) MAGeCK enables robust identification of essential genes from genome-scale CRISPR/Cas9 knockout screens. Genome Biology. 15, 554.

Lissina A., K. Ladell, A. Skowera, M. Clement, E. Edwards, R. Seggwiss, H. van den Berg, E. Gostick, K. Gallagher, E. Jones, J. J. Melenhorst, A. J. Godkin, M. Peakman, D. A. Price, A. K. Sewell and L. Wooldridge (2009) Protein kinase inhibitors substantially improve the physical detection of T-cells with peptide-MHC tetramers. Journal of Immunological Methods, 340, 11-24.

Parra-Cuadrado J F, Navarro P, Mirones I, Setien F, Oteo M, Martinez-Naves E. A study on the polymorphism of human MHC class I-related MR1 gene and identification of an MR1-like pseudogene. Tissue Antigens. 2000; 56(2):170-2.

Patel, S. J. et al 2012 Identification of essential genes for cancer immunotherapy. Nature, 584, 537-542.

R. Reantragoon, A. J. Corbett, I. G. Sakala, N. a Gherardin, J. B. Furness, Z. Chen, S. B. G. Eckle, A. P. Uldrich, R. W. Birkinshaw, O. Patel, L. Kostenko, B. Meehan, K. Kedzierska, L. Liu, D. P. Fairlie, T. H. Hansen, D. I. Godfrey, J. Rossjohn, J. McCluskey, L. Kjer-Nielsen, Antigen-loaded MR1 tetramers define T cell receptor heterogeneity in mucosal-associated invariant T cells. The Journal of experimental medicine. 210, 2305-2320 (2013).

Ryan M. D., A. M. Q. King, G. P. Thomas, (1991) Cleavage of foot-and-mouth disease virus polyprotein is mediated by residues located within a 19 amino acid sequence. Journal of General Virology. 72, 2727-2732.

Sanjana N. E., O. Shalem, F. Zhang, (2014) Improved vectors and genome-wide libraries for CRISPR screening. Nature Methods. 11, 783-784.

Shalem, N. E. Sanjana, E. Hartenian, X. Shi, D. A. Scott, T. S. Mikkelsen, D. Heckl, B. L. Ebert, D. E. Root, J. G. Doench, F. Zhang, (2014) Genome-scale CRISPR-Cas9 knockout screening in human cells. Science. 343, 84-87.

Theaker, S. M., C. Rius, A. Greenshields-Watson, A. Lloyd, A. Trimby, A. Fuller, J. J. Miles, D. K. Cole, M. Peakman and A. K. Sewell G Dolton (2016) T-cell libraries allow simple parallel generation of multiple peptide-specific human T-cell clones. Journal of Immunological Methods 430, 43-50

Tungatt, K., V. Bianchi, M. D. Crowther, W. E. Powell, A. J. Schauenburg, A. Trimby, M. Donia, A. Skowera, J. J. Miles, C. J. Holland, D. K. Cole, A. J. Godkin, M. Peakman, P. T. Straten, I. M. Svane, A. K. Sewell and G, Dolton (2015) Antibody stabilization of peptide-MHC multimers reveals functional T-cells bearing extremely low affinity TCRs. Journal of Immunology 194, 463-74.

Wooldridge L., M. Clement, A. Lissina, E. S. J. Edwards, K. Ladell, J. Ekeruche, R. E. Hewitt, B. Laugel, E. Gostick, D. K. Cole, R. Debets, C. Berrevoets, J. J. Miles, S. R. Burrows, D. A. Price, A. K. Sewell (2010) MHC Class I Molecules with Superenhanced CD8 Binding Properties Bypass the Requirement for Cognate TCR Recognition and Nonspecifically Activate CTLs. The Journal of Immunology. 184, 3357-3366.

Wooldridge L., J. Ekeruche-Makinde, H. A. van den Berg, A. Skowera, J. J. Miles, M. P. Tan, G. Dolton, M. Clement, S. Llewellyn-Lacey, D. A. Price, M. Peakman and A. K. Sewell (2012) A single autoimmune T-cell receptor recognises over a million different peptides. Journal of Biological Chemistry, 287, 1168-77.

The invention claimed is:

1. A vector encoding a T-cell receptor (TCR) that comprises
   a. an α chain that comprises CDR1α, CDR2α, and CDR3α amino acid sequences that are at least 88% identical to the amino acid sequences of SEQ ID Nos: 3, 4, and 1, respectively; and
   b. a β chain that comprises CDR1β, CDR2β, and CDR3β amino acid sequences that are at least 88% identical to the amino acid sequences of SEQ ID Nos: 5, 6, and 2, respectively.

2. The vector of claim 1, wherein
   a. CDR1α comprises the amino acid sequence of SEQ ID NO: 3, CDR2α comprises the amino acid sequence of SEQ ID NO: 4, and CDR3α comprises the amino acid sequence of SEQ ID NO: 1; and
   b. CDR1β comprises the amino acid sequence of SEQ ID NO: 5, CDR2β comprises the amino acid sequence of SEQ ID NO: 6, and CDR3β comprises the amino acid sequence of SEQ ID NO: 2.

3. The vector of claim 1, wherein the α chain comprises an amino acid sequence at least 95% identical to the amino acid sequence of SEQ ID NO: 7.

4. The vector of claim 1, wherein the α chain comprises the amino acid sequence of SEQ ID NO: 7.

5. The vector of claim 1, wherein the β chain comprises an amino acid sequence at least 95% identical to the amino acid sequence of SEQ ID NO: 8.

6. The vector of claim 1, wherein the β chain comprises the amino acid sequence of SEQ ID NO: 8.

7. The vector of claim 1, wherein the α chain comprises an amino acid sequence at least 95% identical to the amino acid sequence of SEQ ID NO: 7; and the β chain comprises an amino acid sequence at least 95% identical to the amino acid sequence of SEQ ID NO: 8.

8. The vector of claim 1, wherein the α chain comprises the amino acid sequence of SEQ ID NO: 7; and the β chain comprises the amino acid sequence of SEQ ID NO: 8.

9. The vector of claim 1, wherein the vector is a lentiviral vector.

10. The vector of claim 1, wherein the TCR is a chimeric TCR.

11. The vector of claim 1, wherein the TCR is MR1-restricted.

12. The vector of claim 1, wherein the TCR is not expressed by mucosal-associated invariant T-cells (MAIT cells).

13. A T-cell comprising the vector of claim 1.

14. A T-cell comprising the vector of claim 2.

15. A T-cell comprising the vector of claim 3.

16. A T-cell comprising the vector of claim 4.

17. A T-cell comprising the vector of claim 5.

18. A T-cell comprising the vector of claim 6.

19. A T-cell comprising the vector of claim 7.

20. A T-cell comprising the vector of claim 8.

21. A T-cell comprising the vector of claim 9.

22. A T-cell comprising the vector of claim 10.

23. A pharmaceutical composition comprising the vector of claim 1.

24. A pharmaceutical composition comprising the T-cell of claim 13.

25. A method of treating cancer in an individual in need thereof, comprising administering to the individual the vector of claim 1.

26. The method of claim 25, wherein the cancer is selected from the group consisting of colorectal cancer, lung cancer, kidney cancer, prostate cancer, cervical cancer, skin cancer, bone cancer, breast cancer, ovarian cancer, and blood cancer.

27. The method of claim 25, wherein the vector is administered in combination with an anti-tumor agent.

28. A method of treating cancer in an individual in need thereof, comprising administering to the individual the T-cell of claim 13.

29. The method of claim 28, wherein the cancer is selected from the group consisting of colorectal cancer, lung cancer, kidney cancer, prostate cancer, cervical cancer, skin cancer, bone cancer, breast cancer, ovarian cancer, and blood cancer.

30. The method of claim 28, wherein the T-cell is administered in combination with an anti-tumor agent.

* * * * *

SEQUENCE LISTING

```
<160> NUMBER OF SEQ ID NOS: 10

<210> SEQ ID NO 1
<211> LENGTH: 13
<212> TYPE: PRT
<213> ORGANISM: Homo sapiens

<400> SEQUENCE: 1

Cys Ala Tyr Arg Ser Ala Val Asn Ala Arg Leu Met Phe
1               5                   10

<210> SEQ ID NO 2
<211> LENGTH: 18
<212> TYPE: PRT
<213> ORGANISM: Homo sapiens

<400> SEQUENCE: 2

Cys Ala Ser Ser Glu Ala Arg Gly Leu Ala Glu Phe Thr Asp Thr Gln
1               5                   10                  15

Tyr Phe

<210> SEQ ID NO 3
<211> LENGTH: 7
<212> TYPE: PRT
<213> ORGANISM: Homo sapiens
```

```
<400> SEQUENCE: 3

Thr Ser Glu Ser Asp Tyr Tyr
1               5

<210> SEQ ID NO 4
<211> LENGTH: 4
<212> TYPE: PRT
<213> ORGANISM: Homo sapiens

<400> SEQUENCE: 4

Ala Thr Glu Asn
1

<210> SEQ ID NO 5
<211> LENGTH: 5
<212> TYPE: PRT
<213> ORGANISM: Homo sapiens

<400> SEQUENCE: 5

Met Gly His Asp Lys
1               5

<210> SEQ ID NO 6
<211> LENGTH: 6
<212> TYPE: PRT
<213> ORGANISM: Homo sapiens

<400> SEQUENCE: 6

Ser Tyr Gly Val Asn Ser
1               5

<210> SEQ ID NO 7
<211> LENGTH: 208
<212> TYPE: PRT
<213> ORGANISM: Artificial
<220> FEATURE:
<223> OTHER INFORMATION: mutant of Homo sapiens

<400> SEQUENCE: 7

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Ala Val Asn Ala Arg Leu Met Phe Gly Asp Gly Thr Gln Leu Val Val
            100                 105                 110

Lys Pro Asn Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
    130                 135                 140

Gln Thr Asn Val Ser Gln Ser Lys Asp Ser Asp Val Tyr Ile Thr Asp
145                 150                 155                 160
```

Lys Cys Val Leu Asp Met Arg Ser Met Asp Phe Lys Ser Asn Ser Ala
            165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
            195                 200                 205

<210> SEQ ID NO 8
<211> LENGTH: 247
<212> TYPE: PRT
<213> ORGANISM: Artificial
<220> FEATURE:
<223> OTHER INFORMATION: mutant of Homo sapiens

<400> SEQUENCE: 8

Glu Ala Asp Ile Tyr Gln Thr Pro Arg Tyr Leu Val Ile Gly Thr Gly
1               5                   10                  15

Lys Lys Ile Thr Leu Glu Cys Ser Gln Thr Met Gly His Asp Lys Met
            20                  25                  30

Tyr Trp Tyr Gln Gln Asp Pro Gly Met Glu Leu His Leu Ile His Tyr
        35                  40                  45

Ser Tyr Gly Val Asn Ser Thr Glu Lys Gly Asp Leu Ser Ser Glu Ser
    50                  55                  60

Thr Val Ser Arg Ile Arg Thr Glu His Phe Pro Leu Thr Leu Glu Ser
65                  70                  75                  80

Ala Arg Pro Ser His Thr Ser Gln Tyr Leu Cys Ala Ser Ser Glu Ala
                85                  90                  95

Arg Gly Leu Ala Glu Phe Thr Asp Thr Gln Tyr Phe Gly Pro Gly Thr
            100                 105                 110

Arg Leu Thr Val Leu Glu Asp Leu Lys Asn Val Phe Pro Pro Glu Val
            115                 120                 125

Ala Val Phe Glu Pro Ser Glu Ala Glu Ile Ser His Thr Gln Lys Ala
        130                 135                 140

Thr Leu Val Cys Leu Ala Thr Gly Phe Tyr Pro Asp His Val Glu Leu
145                 150                 155                 160

Ser Trp Trp Val Asn Gly Lys Glu Val His Ser Gly Val Cys Thr Asp
                165                 170                 175

Pro Gln Pro Leu Lys Glu Gln Pro Ala Leu Asn Asp Ser Arg Tyr Ala
            180                 185                 190

Leu Ser Ser Arg Leu Arg Val Ser Ala Thr Phe Trp Gln Asp Pro Arg
        195                 200                 205

Asn His Phe Arg Cys Gln Val Gln Phe Tyr Gly Leu Ser Glu Asn Asp
    210                 215                 220

Glu Trp Thr Gln Asp Arg Ala Lys Pro Val Thr Gln Ile Val Ser Ala
225                 230                 235                 240

Glu Ala Trp Gly Arg Ala Asp
                245

<210> SEQ ID NO 9
<211> LENGTH: 21
<212> TYPE: DNA
<213> ORGANISM: Homo sapiens

<400> SEQUENCE: 9
gagaccctca ggcggctgct c                                          21

<210> SEQ ID NO 10

```
<211> LENGTH: 24
<212> TYPE: DNA
<213> ORGANISM: Homo sapiens

<400> SEQUENCE: 10
tgtgtggcca ggcacaccag tgtg                                              24
```